US008821599B2

(12) United States Patent
Perkins et al.

(10) Patent No.: US 8,821,599 B2
(45) Date of Patent: Sep. 2, 2014

(54) SYSTEMS AND METHODS FOR BIOMASS GASIFIER REACTOR AND RECEIVER CONFIGURATION

(75) Inventors: Christopher Perkins, Boulder, CO (US); Zoran Jovanovic, Louisville, CO (US); Steven Strand, Midland, MI (US); Donna Kelley, Louisville, CO (US); Andrew Minden, Boulder, CO (US); Richard Ridley, Loveland, CO (US)

(73) Assignee: Sundrop Fuels, Inc., Longmont, CO (US)

( * ) Notice: Subject to any disclaimer, the term of this patent is extended or adjusted under 35 U.S.C. 154(b) by 929 days.

(21) Appl. No.: 12/795,910

(22) Filed: Jun. 8, 2010

(65) Prior Publication Data

US 2010/0247387 A1    Sep. 30, 2010

Related U.S. Application Data

(60) Provisional application No. 61/248,282, filed on Oct. 2, 2009, provisional application No. 61/185,492, filed on Jun. 9, 2009.

(51) Int. Cl.
B01J 7/00     (2006.01)

(52) U.S. Cl.
USPC ............................................................ 48/61

(58) Field of Classification Search
None
See application file for complete search history.

(56) References Cited

U.S. PATENT DOCUMENTS

| 1,508,464 A | 9/1924 | McFarland |
| 2,237,491 A | 4/1941 | Kutz |
| 4,164,123 A | 8/1979 | Smith |
| 4,219,492 A | 8/1980 | Konoki et al. |
| 4,247,755 A | 1/1981 | Smith, Jr. et al. |
| 4,415,339 A | 11/1983 | Aiman et al. |
| 4,455,153 A | 6/1984 | Jakahi |
| 4,552,741 A | 11/1985 | Melchoir |
| 4,704,137 A | 11/1987 | Richter |
| 4,756,722 A | 7/1988 | Knop et al. |
| 4,766,154 A | 8/1988 | Bonnell et al. |
| 5,179,129 A | 1/1993 | Studer |
| 5,581,998 A | 12/1996 | Craig |
| 5,618,500 A | 4/1997 | Wang |
| 5,647,877 A | 7/1997 | Epstein |

(Continued)

FOREIGN PATENT DOCUMENTS

| JP | 2002/012877 A | 1/2002 |
| SU | 1763814 A1 | 9/1992 |

(Continued)

OTHER PUBLICATIONS

International Preliminary Report on Patentability for International Application No. PCT/US10/37911, dated Dec. 12, 2011, 9 pages.

(Continued)

*Primary Examiner* — Imran Akram
(74) *Attorney, Agent, or Firm* — Rutan & Tucker, LLP

(57) ABSTRACT

A method, apparatus, and system for solar-driven chemical plant may include a solar thermal receiver to absorb concentrated solar energy from an array of heliostats. Additionally, some embodiments may include a solar driven chemical reactor that has multiple reactor tubes. The concentrated solar energy drives the endothermic gasification reaction of the particles of biomass flowing through the reactor tubes. Some embodiments may also include an on-site fuel synthesis reactor that is geographically located on the same site as the chemical reactor and integrated to receive the hydrogen and carbon monoxide products from the gasification reaction.

14 Claims, 9 Drawing Sheets

(56) References Cited

U.S. PATENT DOCUMENTS

| | | | |
|---|---|---|---|
| 5,906,799 A | 5/1999 | Burgie et al. |
| 6,402,988 B1 | 6/2002 | Gottzmann et al. |
| 6,660,244 B2 | 12/2003 | Negishi et al. |
| 6,676,716 B2 | 1/2004 | Fujimura et al. |
| 6,872,378 B2 | 3/2005 | Weimer et al. |
| 7,033,570 B2 | 4/2006 | Weimer et al. |
| 7,207,327 B2 | 4/2007 | Litwin et al. |
| 7,553,476 B2 | 6/2009 | Marrella et al. |
| 7,632,476 B2 | 12/2009 | Shah et al. |
| 7,686,856 B2 | 3/2010 | Hemmings et al. |
| 7,856,829 B2 | 12/2010 | Shah et al. |
| 7,871,457 B2 | 1/2011 | Shah et al. |
| 7,881,825 B2 | 2/2011 | Esposito et al. |
| 7,931,888 B2 | 4/2011 | Drnevich et al. |
| 7,985,399 B2 | 7/2011 | Drnevich et al. |
| 8,007,761 B2 | 8/2011 | Drnevich et al. |
| 8,378,151 B2 | 2/2013 | Perkins |
| 2002/0134019 A1 | 9/2002 | Paisley |
| 2003/0182861 A1 | 10/2003 | Weimer et al. |
| 2003/0208959 A1 | 11/2003 | Weimer et al. |
| 2003/0213514 A1 | 11/2003 | Ortabasi |
| 2004/0170210 A1 | 9/2004 | Do et al. |
| 2004/0219079 A1 | 11/2004 | Hagen et al. |
| 2005/0020700 A1 | 1/2005 | Bahnisch |
| 2005/0142049 A1 | 6/2005 | Amsden et al. |
| 2006/0024538 A1 | 2/2006 | Steinberg |
| 2006/0096298 A1 | 5/2006 | Barnicki et al. |
| 2006/0140848 A1 | 6/2006 | Weimer et al. |
| 2006/0188433 A1 | 8/2006 | Weimer et al. |
| 2006/0225424 A1 | 10/2006 | Elliot et al. |
| 2007/0098602 A1 | 5/2007 | Haueter et al. |
| 2007/0129450 A1 | 6/2007 | Barnicki et al. |
| 2007/0225382 A1 | 9/2007 | Van Den Berg et al. |
| 2008/0025884 A1 | 1/2008 | Tonkovich et al. |
| 2008/0057366 A1 | 3/2008 | Katikaneni et al. |
| 2008/0086946 A1 | 4/2008 | Weimer et al. |
| 2008/0104003 A1 | 5/2008 | Macharia et al. |
| 2008/0209891 A1 | 9/2008 | Johannes et al. |
| 2008/0222955 A1 | 9/2008 | Jancker et al. |
| 2008/0223214 A1 | 9/2008 | Palamara et al. |
| 2008/0284401 A1 | 11/2008 | Oettinger et al. |
| 2008/0293132 A1 | 11/2008 | Goldman et al. |
| 2008/0302670 A1 | 12/2008 | Boyle |
| 2008/0307703 A1 | 12/2008 | Dietenberger |
| 2009/0013601 A1 | 1/2009 | Mandich et al. |
| 2009/0014689 A1 | 1/2009 | Klepper et al. |
| 2009/0018221 A1 | 1/2009 | Klepper et al. |
| 2009/0018222 A1 | 1/2009 | Klepper et al. |
| 2009/0018371 A1 | 1/2009 | Klepper et al. |
| 2009/0018372 A1 | 1/2009 | Tirmizi et al. |
| 2009/0064578 A1 | 3/2009 | Theegala |
| 2009/0069452 A1 | 3/2009 | Robota |
| 2009/0069609 A1 | 3/2009 | Kharas et al. |
| 2009/0093555 A1 | 4/2009 | Stites et al. |
| 2009/0151251 A1 | 6/2009 | Manzer et al. |
| 2009/0151253 A1 | 6/2009 | Manzer et al. |
| 2009/0156392 A1 | 6/2009 | Kharas |
| 2009/0156393 A1 | 6/2009 | Kharas |
| 2009/0156697 A1 | 6/2009 | Kharas |
| 2009/0313886 A1 | 12/2009 | Hinman |
| 2009/0318573 A1 | 12/2009 | Stites et al. |
| 2010/0000874 A1 | 1/2010 | Hinman |
| 2010/0022806 A1 | 1/2010 | Meitzner |
| 2010/0075837 A1 | 3/2010 | Meitzner et al. |
| 2010/0076228 A1 | 3/2010 | Alsum et al. |
| 2010/0099925 A1 | 4/2010 | Kharas |
| 2010/0099926 A1 | 4/2010 | Kharas |
| 2010/0099927 A1 | 4/2010 | Kharas |
| 2010/0137459 A1 | 6/2010 | Stites et al. |
| 2010/0152497 A1 | 6/2010 | Stites |
| 2010/0152498 A1 | 6/2010 | Kharas et al. |
| 2010/0210741 A1 | 8/2010 | Kharas |
| 2010/0212220 A1 | 8/2010 | Tirmizi |
| 2010/0237291 A1 | 9/2010 | Simmons |
| 2010/0242352 A1 | 9/2010 | Perkins |
| 2010/0242353 A1 | 9/2010 | Jovanovic |
| 2010/0242354 A1 | 9/2010 | Perkins |
| 2010/0243961 A1 | 9/2010 | Hilton |
| 2010/0247387 A1 | 9/2010 | Perkins et al. |
| 2010/0249251 A1 | 9/2010 | Hilton |
| 2010/0249468 A1 | 9/2010 | Perkins et al. |
| 2010/0270505 A1 | 10/2010 | Gallaspy et al. |
| 2010/0273899 A1 | 10/2010 | Winter |
| 2010/0280287 A1 | 11/2010 | Kharas et al. |
| 2010/0303692 A1 | 12/2010 | Perkins |
| 2010/0331581 A1 | 12/2010 | Kharas et al. |
| 2011/0107661 A1 | 5/2011 | Tirmizi et al. |
| 2011/0107662 A1 | 5/2011 | Tirmizi et al. |
| 2011/0107663 A1 | 5/2011 | Tirmizi et al. |
| 2011/0124927 A1 | 5/2011 | Stites et al. |
| 2011/0155958 A1 | 6/2011 | Winter et al. |
| 2011/0301732 A1 | 12/2011 | Gao et al. |
| 2012/0145965 A1 | 6/2012 | Simmons |
| 2012/0181483 A1 | 7/2012 | Perkins et al. |
| 2012/0241677 A1 | 9/2012 | Perkins |

FOREIGN PATENT DOCUMENTS

| | | | |
|---|---|---|---|
| WO | WO 2010/144537 A1 | 12/2010 |
| WO | WO 2010/144549 A1 | 12/2010 |
| WO | WO 2010/144552 A1 | 12/2010 |
| WO | WO 2010/144556 A1 | 12/2010 |
| WO | WO 2010/144537 A9 | 2/2011 |
| WO | WO 2011/155962 A1 | 12/2011 |

OTHER PUBLICATIONS

International Preliminary Report on Patentability for International Application No. PCT/US10/37914, dated Dec. 12, 2011, 8 pages.
International Preliminary Report on Patentability for International Application No. PCT/US10/37923, dated Dec. 12, 2011, 13 pages.
International Preliminary Report on Patentability for International Application No. PCT/US10/37925, dated Dec. 12, 2011, 10 pages.
International Preliminary Report on Patentability for International Application No. PCT/US10/37930, dated Dec. 12, 2011, 13 pages.
International Preliminary Report on Patentability for International Application No. PCT/US10/37934, dated Dec. 12, 2011, 10 pages.
International Preliminary Report on Patentability for International Application No. PCT/US10/37938, dated Dec. 12, 2011, 10 pages.
International Preliminary Report on Patentability for International Application No. PCT/US10/37940, dated Dec. 12, 2011, 10 pages.
International Preliminary Report on Patentability for International Application No. PCT/US10/37944, dated Dec. 12, 2011, 10 pages.
Cross Reference to Related Applications Under 27 C.F.R. 1.78, 2 pages.
International Search Report for PCT/US10/037911, dated Aug. 6, 2010, 2 pages.
International Search Report for PCT/US10/037914, dated Aug. 13, 2010, 2 pages.
International Search Report for PCT/US10/037923, dated Aug. 9, 2010, 3 pages.
International Search Report for PCT/US10/037925, dated Aug. 10, 2010, 3 pages.
International Search Report for PCT/US10/037930, dated Sep. 20, 2010, 5 pages.
International Search Report for PCT/US10/037934, dated Aug. 9, 2010, 2 pages.
International Search Report for PCT/US10/037938, dated Aug. 5, 2010, 2 pages.
International Search Report for PCT/US10/037940, dated Aug. 13, 2010, 2 pages.
International Search Report for PCT/US10/037944, dated Aug. 18, 2010, 2 pages.
Munzinger, M., et al., "Biomass Gass ification Using Solar Thermal Energy", *Anzses 2006*, pp. 1-10.
Mishra, Anuradha, et al., "Thermal Optimization of Solar Biomass Hybrid Cogeneration Plants", *Journal of Scientific & Industrial Research*, vol. 65, Apr. 2006, pp. 355-363.

(56) References Cited

OTHER PUBLICATIONS

Esser, Peter, et al., "The Photochemical Synthesis of Fine Chemicals With Sunlight," Angew. Chem. Int. Ed. Engl. 1994, vol. 33, pp. 2009-2023.

Bridgwater, et al., "Fast Pyrolysis Processes for Biomass," Renewable and Sustainable Energy Reviews, vol. 4, No. 1, 73 pages, Mar. 2000.

Lede, "Solar Thermochemical Conversion of Biomass", Solar Energy, vol. 65, No. 1, 11 pages, Jan. 1, 1999.

*Netscape Communications Corp.* v. *ValueClick, Inc.*, 684 F. Supp. 2d. 678—Dist. Court, ED Virginia 2010. No. 1 :09cv225. United States District Court, E. D. Virginia, Alexandria Division. Oct. 22, 2009. 38 pages.

*Ex Parte* Wada and Murphy, U.S. Patent and Trademark Office Board of Patent Appeals and Interferences Decision on Appeal dated Jan. 14, 2008, 9 pages.

*Ex Parte* Chapman, U.S. Patent and Trademark Office Board of Patent Appeals and Interferences Decision on Appeal dated Feb. 9, 2012 for Appeal No. 2009-010238, U.S. Appl. No. 10/751,616, 6 pages.

Higuchi, Takayoshi "Steam Explosion of Wood", Sections 1-4, Biomass Handbook, © 1989 by OPA (Amsterdam), pp. 470-473 plus Cover, Biblio, Table of Contents excerpt. 7 pages total, Editors: Osamu Kitani & Carl W. Hall, ISBN 2-88124-269-3, Gordon and Breach Science Publishers S. A., Cooper Station, New York, New York.

"StakeTech—First Pulping System Receives Full Acceptance", May 14, 1996, 2 pages. Publisher: Business Wire. downloaded from http://www.thefreelibrary.com/StakeTech.

McCallum, Don, "Medium Density Fiber Board" pp. 8-11, Nov. 1, 1996 http://fennerschool-associated.anu.edu.au/fpt/manufacture.html.

Restriction Requirement for U.S. Appl. No. 12/796,045 mailed Apr. 18, 2013, 5 p. U.S. Patent and Trademark Office, Alexandria VA US.

Non-Final Office Action for U.S. Appl. No. 12/796,045 mailed Sep. 13, 2013, 15 p. U.S. Patent and Trademark Office, Alexandria VA US.

Non-Final Office Action for U.S. Appl. No. 12/796,121 mailed Jun. 7, 2012, 10 p., U.S. Patent and Trademark Office, Alexandria VA US.

Notice of Allowance for U.S. Appl. No. 12/796,121 mailed Oct. 11, 2012, 7 p., U.S. Patent and Trademark Office, Alexandria VA US.

Restriction Requirement for U.S. Appl. No. 12/796,471 mailed Mar. 13, 2013, 6 p. U.S. Patent and Trademark Office, Alexandria VA US.

Non-Final Office Action for U.S. Appl. No. 12/796,471 mailed May 3, 2013, 22 p. U.S. Patent and Trademark Office, Alexandria VA US.

Final Office Action for U.S. Appl. No. 12/796,471 mailed Nov. 27, 2013, 26 p. U.S. Patent and Trademark Office, Alexandria VA US.

Restriction Requirement for U.S. Appl. No. 13/254,020 mailed Nov. 26, 2012, 6 p. U.S. Patent and Trademark Office, Alexandria VA US.

Non-Final Office Action for U.S. Appl. No. 13/254,020 mailed May 9, 2013, 21 p. U.S. Patent and Trademark Office, Alexandria VA US.

Final Office Action for U.S. Appl. No. 13/254,020 mailed Oct. 29, 2013, 23 p. U.S. Patent and Trademark Office, Alexandria VA US.

Multiple tube reactor

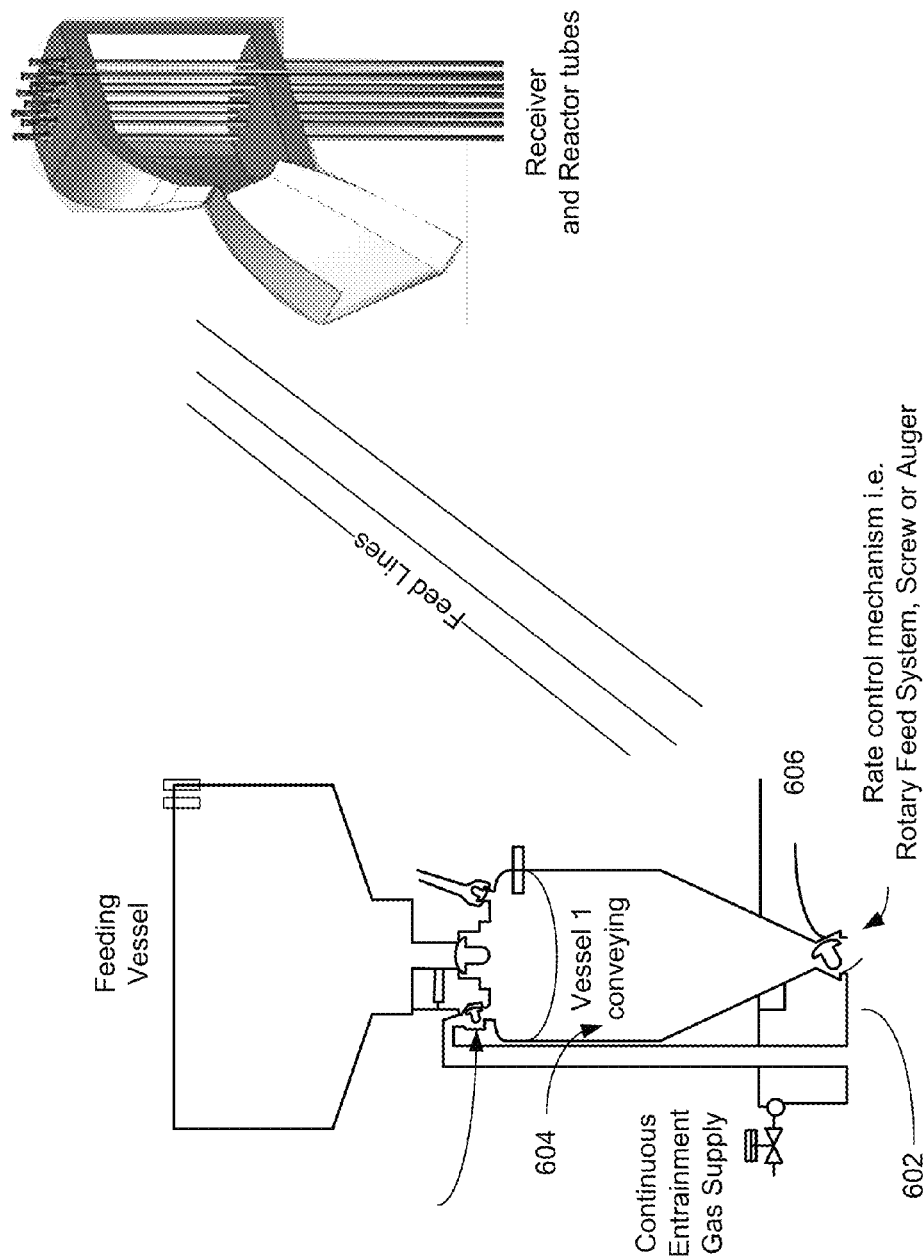

SYSTEMS AND METHODS FOR BIOMASS GASIFIER REACTOR AND RECEIVER CONFIGURATION

RELATED APPLICATIONS

This application claims the benefit of both U.S. Provisional Patent Application Ser. No. 61/248,282, filed Oct. 2, 2009 and entitled "Various Methods and Apparatuses for Sun Driven Processes," and U.S. Provisional Patent Application Ser. No. 61/185,492, titled "VARIOUS METHODS AND APPARATUSES FOR SOLAR-THERMAL GASIFICATION OF BIOMASS TO PRODUCE SYNTHESIS GAS" filed Jun. 9, 2009.

NOTICE OF COPYRIGHT

A portion of the disclosure of this patent document contains material that is subject to copyright protection. The copyright owner has no objection to the facsimile reproduction by anyone of the software engine and its modules, as it appears in the Patent and Trademark Office Patent file or records, but otherwise reserves all copyright rights whatsoever.

FIELD OF THE INVENTION

Embodiments of the invention generally relate to systems, methods, and apparatus for refining biomass and other materials. More particularly, an aspect of an embodiment of the invention relates to solar-driven systems, methods, and apparatus for refining biomass and other materials.

BACKGROUND OF THE INVENTION

The substance/substances initially involved in a chemical reaction are generally called reactants. Chemical reactions are usually characterized by a chemical change in the reactants, which then yields one or more products. Biomass gasification is an endothermic process that generates syngas; energy must be put into the process to drive the chemical reaction forward. Typically, this is performed by partially oxidizing (burning) the biomass itself. Between 30% and 40% of the biomass must be consumed to drive the process, and at the temperatures which the process is generally limited to (for efficiency reasons), conversion is typically limited, giving still lower yields and producing tars. Also, the chemical reactors in such traditional biorefineries are generally engineered to operate at constant conditions around the clock. In contrast, the proposed solar-driven biorefinery uses an external source of energy (solar) to provide the energy required for reaction, so none of the biomass need be consumed to achieve the conversion. This results in significantly higher yields of gallons of gasoline per biomass ton than previous technologies. As such, the energy source being used to drive the conversion is renewable and carbon free.

SUMMARY OF THE INVENTION

Some embodiments relate to a method, apparatus, and system for solar-driven chemical plant may include a solar thermal receiver to absorb concentrated solar energy from an array of heliostats. Additionally, some embodiments may include a solar driven chemical reactor that has multiple reactor tubes. These tubes can be in a downdraft geometry located inside the solar thermal receiver. Additionally, inside the multiple reactor tubes, particles of biomass may be gasified in the presence of a carrier gas. This gasification process is endothermic, and may produce hydrogen and carbon monoxide products at an exit temperature from the tubes exceeding 1000 degrees C.

In some embodiments, one or more apertures 1) open to an atmosphere of the Earth or 2) covered by a window, may be used to pass the concentrated solar energy into the solar thermal receiver. This energy may impinge on the multiple reactor tubes and the internal cavity walls of the receiver. Accordingly, the reactor tubes may serve the dual functions of 1) segregating the biomass gasification reaction environment from the atmosphere of the Earth and 2) transferring energy by solar radiation absorption and heat radiation, convection, and conduction to the reacting particles. This can drive the endothermic gasification reaction of the particles of biomass flowing through the reactor tubes. Additionally, high heat transfer rates of the materials making up the cavity walls and the reactor tubes may allow the particles biomass to achieve a high enough temperature necessary for substantial tar destruction and complete gasification of greater than 90 percent of the carbon content of the particles into reaction products including hydrogen and carbon monoxide gas in a very short residence time between a range of 0.01 and 5 seconds.

Some embodiments may also include an on-site fuel synthesis reactor that may be geographically located on the same site as the solar chemical reactor and integrated to receive the hydrogen and carbon monoxide products from the gasification reaction. The on-site fuel synthesis reactor may be configured to use the hydrogen and carbon monoxide products in a hydrocarbon fuel synthesis process to create a liquid hydrocarbon fuel.

BRIEF DESCRIPTION OF THE DRAWINGS

The drawings refer to embodiments of the invention in which:

FIGS. 6a and 6b illustrate block diagrams of embodiments of the entrained-flow biomass feed system;

Figure 1:
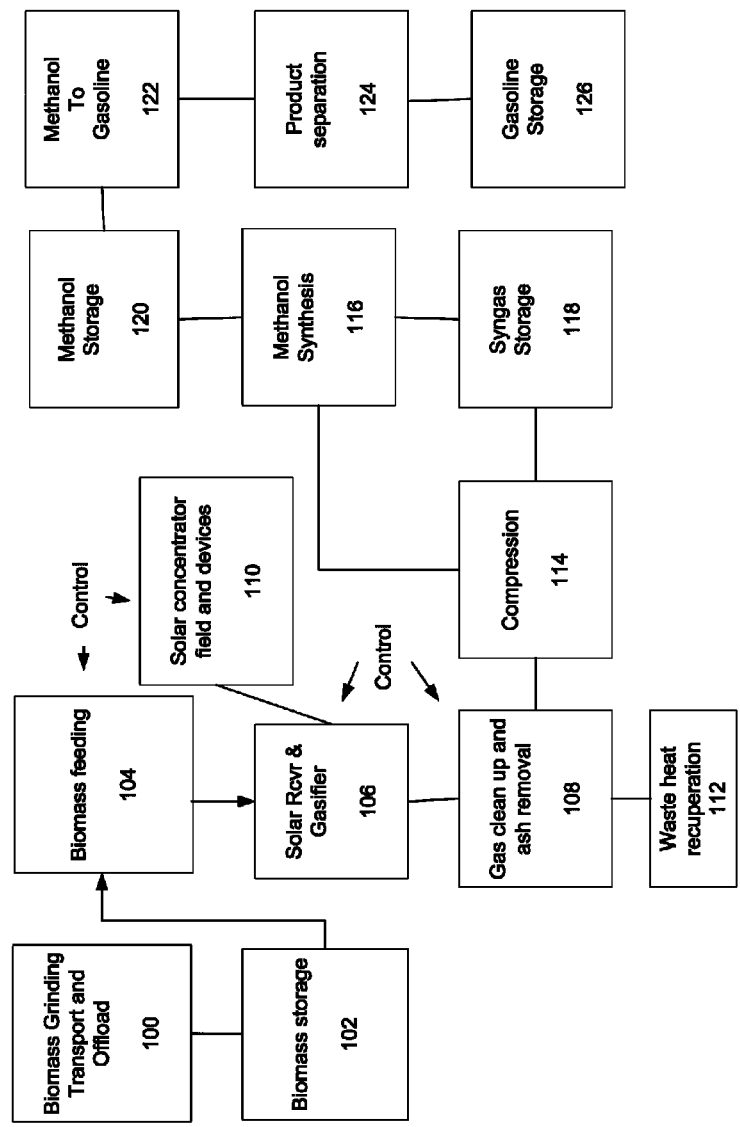
FIG. 1 illustrates a block diagram of an embodiment of an example process flow.

While the invention is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the invention.

DETAILED DISCUSSION

In the following description, numerous specific details are set forth, such as examples of specific data signals, named components, connections, number of reactor tubes, etc., in order to provide a thorough understanding of the present invention. It will be apparent, however, to one of ordinary skill in the art that the present invention may be practiced without these specific details. In other instances, well known components or methods have not been described in detail but rather in a block diagram in order to avoid unnecessarily obscuring the present invention. Further specific numeric references such as first reactor tube, may be made. However, the specific numeric reference should not be interpreted as a literal sequential order but rather interpreted that the first reactor tube is different than a second reactor tube. Thus, the specific details set forth are merely exemplary. The specific details may be varied from and still be contemplated to be within the spirit and scope of the present invention. Features found in one embodiment may generally be used in another embodiment. The term coupled is defined as meaning connected either directly to the component or indirectly to the component through another component.

In general, the solar-driven chemical plant includes an entrained-flow biomass feed system feeding a chemical reactor that is feedstock flexible via at least particle size control of the biomass. One example system includes the chemical reactor that supplies an on-site fuel synthesis reactor. The chemical reactor may receive concentrated solar thermal energy from an array of heliostats and this energy can be used to drive chemical reactions including a gasification reaction of the biomass. A solar thermal receiver may also be aligned to absorb concentrated solar energy from the array of heliostats.

The solar driven chemical reactor may have multiple reactor tubes. These tubes can be in a downdraft geometry located inside the solar thermal receiver. Additionally, inside the multiple reactor tubes particles of biomass may be gasified in the presence of a carrier gas. This may be done in an endothermic gasification reaction to produce hydrogen and carbon monoxide products at an exit temperature from the tubes exceeding 1000 degrees C.

The concentrated solar energy may impinge on the multiple reactor tubes and the internal cavity walls of the receiver. Accordingly, the reactor tubes may serve the dual functions of 1) segregating the biomass gasification reaction environment from the atmosphere of the solar thermal receiver and 2) transferring energy by solar radiation absorption and heat radiation, convection, and conduction to the reacting particles. This can drive the endothermic gasification reaction of the particles of biomass flowing through the reactor tubes. Additionally, high heat transfer rates of the materials making up the cavity walls and the reactor tubes may allow the particles biomass to achieve a high enough temperature necessary for substantial tar destruction and complete gasification of greater than 90 percent of the particles into reaction products including hydrogen and carbon monoxide gas in a very short residence time between a range of 0.01 and 5 seconds.

The carbonaceous biomass material particles being fed from the entrained flow biomass feed system undergo several distinct chemical processes of the gasification reaction prior to exiting the reactor tubes including the following.

In some embodiments, one or more apertures with or without windows are part of a receiver outer shell that at least partially encloses the multiple reactor tubes. The inside wall of the receiver shell may absorb or highly reflect the concentrated solar energy. This can cause a radiant heat and then generally radiatively convey that heat to the biomass particles in the tubes of the solar driven chemical reactor. Additionally, an inner wall of the receiver cavity may be made of material to allow the receiver cavity to be operated at high (>1200° C.) wall temperatures to enable the high heat transfer rates, rapid reaction kinetics, and high selectivity to syngas.

Additionally, some embodiments may include an opaque outer wall for each of the reactor tubes. An inner wall of the receiver and the reactor tubes may exchange energy primarily by radiation, not by convection or conduction, in such an embodiment. This can allow for the reactor tubes to achieve a fairly uniform temperature profile even though the concentrated solar energy from the heliostat array or solar concentrators is merely directly impinging on the reactor tubes from one direction. The radiation heat transfer from the inner wall and the reactor tubes may be the primary source of energy driving the gasification reaction in which the small biomass particles act as millions of tiny absorbing surfaces of radiant heat energy coming from the inner wall and the tubes.

FIG. 1 illustrates a block diagram of an example process flow. Some embodiments encompass a solar-driven-biomass gasification to liquid fuel/electrical process. In a specific example implementation the process described is a solar-driven-biomass gasification to 'green' liquid fuel process. In an embodiment, this process includes one or more of the following process steps.

Biomass grinding or densification, transport and offload 100 may be part of the overall process. Bales of the biomass can be compressed and densified by a compactor to facilitate transport to on-site via the densification achieved by the compression and the bales are sized to dimensions that may, for example, fit within a standard box car size or shipping container size, or fit within standard compactor size. The entrained-flow biomass feed system can be preceded by a grinding system equipped with mechanical cutting device and a particle classifier, such as a perforated screen or a cyclone, to control the size of the particles. The biomass may be in an embodiment non-food stock biomass. In some cases, food stock biomass might also be processed.

The biomass may then be stored 102. As needed, the biomass might be fed 104 into an example system or apparatus of the instant application. For example, after grinding and pulverizing the biomass to particles, the particles of biomass can be fed into and gasified in the solar-driven chemical reactor. Two or more feed lines supply the particles of biomass having an average smallest dimension size between 50 microns (um) and 2000 um to the chemical reactor.

A solar receiver and gasifier 106 may be used to gasify the biomass. An example biomass gasifier design and operation can include a solar chemical reactor and solar receiver to generate the syngas. The chemical reactor's configuration, dimensions, shape, and material may be varied as well as its cooperation with its solar receiver. Both the chemical reactor and solar receiver form the solar receiver and gasifier 106. Various heliostat field designs and operations to drive the biomass gasifier might be used. Some example systems may include a solar concentrator, secondary concentrator, focused mirror array, etc. to drive biomass gasifier 110.

Quenching, gas clean up, and ash removal from biomass gasifier 108 may be provided for. Some gasses may be a waste product, while other gasses can be compressed 114 prior to storage 118 or e.g., methanol synthesis 116. Methanol may then be stored 120 for later methanol to gasoline conversion 122.

In various embodiments, synthesis gas may be fed to another technical application. Examples include a syngas to other chemical conversion process. The other chemical of chemicals produced can include liquefied fuels such as transportation liquefied fuels. In an example hydrocarbon based fuel, Methanol 116 may be formed from syngas. The methanol may be further concerted to gasoline or other fuels 122 and various products may be separated out from the gasoline 124 or syngas. These products, e.g., gasoline, may then be stored for later use as an energy source.

Some embodiments can include the on-site chemical synthesis reactor, such as a fuel synthesis reactor, that may be geographically located on the same site as the chemical reactor and integrated to receive the hydrogen and carbon monoxide products from the gasification reaction. The on-site fuel synthesis reactor has an input to receive the hydrogen and carbon monoxide products and use them in a hydrocarbon fuel synthesis process to create a liquid hydrocarbon fuel.

The on-site fuel synthesis reactor may be connected to the rest of the plant facility by a pipeline that is generally less than 15 miles in distance. The on-site fuel synthesis reactor may supply various feedback parameters and other request to the control system. For example, the on-site fuel synthesis reactor can request the control system to alter the H2 to CO ratio of the syngas coming out of the quenching and gas clean up portion of the plant and the control system will do so.

Some embodiments of the systems and methods described herein can include a controller, such as a computerized controller. The tuning and predictive parameters for this controller may be optimized for the full-scale receiver/reactor system, where lag times and response parameters of the heliostat array's flux at the aperture, change in flow rate of the biomass thermal mass are taken in account. The tuning and predictive parameters may also set for the control system tuning parameters at peak, mid, and trough solar energy conditions, as well as operation of the control system with +/−10% temperature set point through 10 typical solar days.

Figure 2:
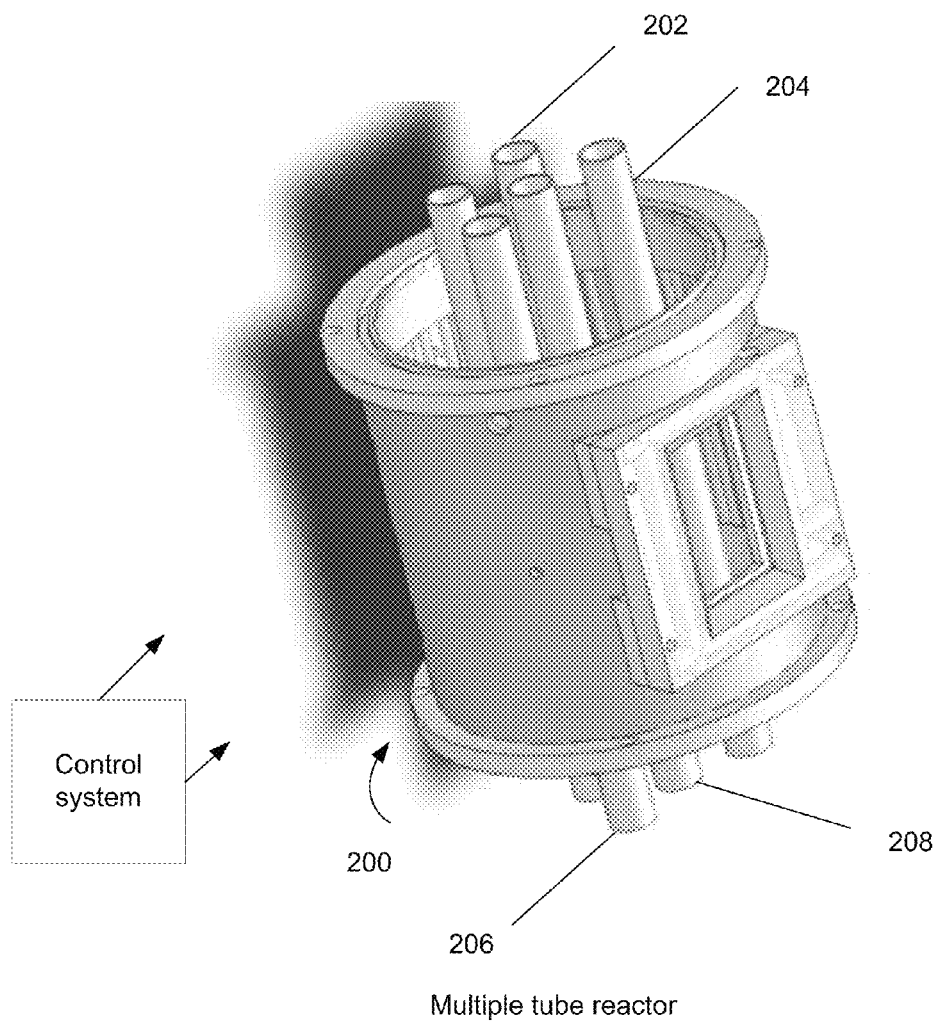
FIG. 2 illustrates a diagram of an embodiment of an example multiple tube reactor.

FIG. 2 illustrates a diagram of an example multiple tube chemical reactor that may be used in a solar driven system. Reactor has multiple reactor tubes 202, 204, 206, 208 and a separate entrainment line may be used for each of the gasifier reactor tubes 202, 204, 206, 208 in the chemical reactor 200. This may allow for independent temperature control and balancing of amount of particles of biomass flowing in each of the reactor tubes 202, 204, 206, 208 in the multiple tube solar driven chemical reactor 200. An example amount of five reactor tubes 202, 204, 206, 208 is shown. The particles of biomass feed can be distributed to the reactor tubes 202, 204, 206, 208 by a lock hopper rotary feed system, such as a Rotofeed® lock hopper rotary feed system. Such a system can allow for balanced feeding to individual reactor tubes 202, 204, 206, 208 and feed rate of the particles is controlled by controlling the rotational speed of the Rotofeed® based on weight change of the biomass in the lock hopper monitored by device such as load cells.

A solar-driven bio-refinery can include a solar thermal receiver 200 aligned to absorb concentrated solar energy from an array of heliostats, a set of solar concentrating dishes, or a combination of both. The receiver 200 is the cavity that collects and distributes the solar energy, while the reactors tubes are the individual transport tubes in which the chemical reactions take place. The receiver cavity is the insulating surroundings in which the reactor tubes sit. The reactor tubes are the tubes through which the biomass may flow and then in which the gasification reaction takes place.

Various embodiments can include a biomass gasifier reactor and receiver configuration that can include various reactor dimensions, shape, and material. For example, a solar driven chemical reactor that has multiple reactor tubes 202, 204, 206, 208 in a downdraft geometry may be used. The multiple reactor tubes 202, 204, 206, 208 can be located inside the solar thermal receiver 200. In the multiple reactor tubes 202, 204, 206, 208 particles of biomass may be gasified in the presence of a carrier gas in an endothermic gasification reaction to produce hydrogen and carbon monoxide products at an exit temperature from the tubes exceeding 1000 degrees C.

In some embodiments, one or more apertures open to an atmosphere of the Earth or covered with a window may be used to pass concentrated solar energy into the solar thermal receiver 200 to impinge on the multiple reactor tubes 202, 204, 206, 208 and cavity walls of the receiver 200. The reactor tubes 202, 204, 206, 208 serve the dual functions of 1) segregating the biomass gasification reaction environment from the atmosphere of the Earth and 2) transferring energy by solar radiation absorption and re-radiation, convection, and conduction. This energy is transferred to the reacting particles to drive the endothermic gasification reaction of the particles of biomass flowing through the reactor tubes 202, 204, 206, 208. High heat transfer rates from the materials making up the cavity walls and the reactor tubes 202, 204, 206, 208 may allow the particles biomass to achieve a high enough temperature necessary for substantial tar destruction and complete gasification of greater than 90 percent of the carbon content of the particles into reaction products including hydrogen and carbon monoxide gas in a very short residence time between a range of 0.01 and 5 seconds.

Each of the multiple reactor tubes 202, 204, 206, 208 may provide a chamber for a chemical reaction driven by radiant heat to occur. Additionally, the multiple reactor tubes 202, 204, 206, 208 in this reactor design increase available reactor surface area for radiative exchange to the reactants and inter-tube radiation exchange. The chemical reaction may include one of biomass gasification, steam methane reforming, methane cracking, steam methane cracking to produce ethylene, metals refining, and CO2 capture can be conducted in this reactor using solar thermal energy.

An example solar-driven chemical plant has a top of the multiple reactor tubes 202, 204, 206, 208. The tubes are oriented vertically in the solar receiver cavity. The biomass particles are introduced at the top of the reactor tubes 202, 204, 206, 208, entrained by the carrier gas such as steam, and are directed by gravity and pressure through a gasification reaction zone of the reactor tubes 202, 204, 206, 208. Temperatures of operation can be clearly delineated with the receiver cavity wall temperatures between 1100 degrees C. and 1450 degrees C. and a gas temperature from an exit of the gasification reaction zone of the reactor tubes 202, 204, 206, 208 is in excess of 1000 degrees C. Some embodiments use reactor tubes 202, 204, 206, 208 operating at temperatures of good reactor efficiency that are not above the silica melting temperature of 1600 degrees C.

In some embodiments, the solar-driven chemical plant includes reactor tubes 202, 204, 206, 208 with an inner diameter sized to allow a substantially uniform gasification of biomass particles from the edges to the center of the tube. Some have a wall thickness set to withstand at least a 75 psig pressure at 1400° C. on the inside tube walls.

The one or more apertures may be part of the receiver's outer shell that at least partially encloses multiple reactor tubes 202, 204, 206, 208. The receiver's shell may absorb or highly reflect the concentrated solar energy to cause a radiant heat and then generally radiatively convey that heat to the biomass particles in the tubes of the solar driven chemical reactor. Additionally, an inner wall of the receiver cavity may be made of material to allow the receiver cavity to be operated at high (>1200° C.) wall temperatures. This can enable the high heat transfer rates, rapid reaction kinetics of the very short residence time, and high selectivity of carbon monoxide and hydrogen produced from the gasification reaction for syngas.

Note, a chemical reactor is the container in which a chemical reaction occurs. Also, the chemical reactor may be a single reactor tube, or a set of reactor tubes. Thus, the chemical reactor may be a single reactor with multiple reactor tubes or multiple reactors each being a single reactor tube, or some other similar combination. Further, different chemical reactions may take place in different reactor tubes of the solar-driven chemical reactor. For example, Steam Methane Reforming may occur in a first set of reactor tubes and biomass gasification may occur in another set of reactor tubes making up the chemical reactor, which is at least partially contained in the solar thermal receiver. Also, different reactions such as SMR and biomass gasification may occur at the same time within the same reactor tube. Additionally, the control system may control the chemical reactions occurring within the reactor tubes via a number mechanisms as described herein. For example, the flow rate of the chemical reactants, such as biomass particles and carrier gas, into and through the reactor tubes is controlled, along with a concentration of each reactant flowing through the reactor tube. The control system may control each reactor tube individually, or in sets/groups of for example clusters of eighteen tubes, or all of the tubes in their entirety. The shape, orientation, and other features of the reactor tubes may vary as described herein. Note, for contrast purposes, more than one chemical reactor may be located on a common tower such as in FIG. 3. The example shows a first chemical reactor, a second chemical reactor, and a third chemical reactor contained at least partially within its own associated solar thermal receiver. The first, second, and third chemical reactors located on the same tower may not share a common control system or common solar thermal receiver, and thus, are truly each distinct chemical reactors. However, they all may be fed from some common feed vessels/lock hoppers and/or may share downstream quenching and gas clean up system components.

In the multiple reactor tubes of the chemical reactor a chemical reaction driven by radiant heat occurs. The chemical reaction includes one or more of biomass gasification, steam methane reforming, methane cracking, steam methane cracking to produce ethylene, metals refining, and CO2 or H2O splitting to be conducted in this chemical reactor using solar thermal energy from the absorbed concentrated solar energy. A first set of tubes may have a steam methane reforming reaction occurring while a second set of tubes has a biomass gasification reaction occurs.

Biomass gasification takes place through a number of complex reactions, but these can be grouped into a couple of broad groups. In the first group, volatile components (hydrogen, light alkanes and alkenes) are released at relatively low temperature (200° C.-600° C.). The reactions are primarily endothermic, and in a falling particle reactor these initial reactions will likely be driven at these low temperatures due to heat transfer limitations. As the reactions proceed, oxygen-deficient char is left behind, in large part from lignin. This component requires higher temperatures (>800° C.) and an oxidant to gasify. Additionally, the heavier volatile products (tars) from the first series of reactions will break down further into CO and H2 at high temperatures (1000° C.-1200° C.).

Thus, the carbonaceous biomass material particles being fed from the entrained flow biomass feed system undergoes several distinct chemical processes of the gasification reaction prior to exiting the reactor tubes including the following. 1) Initially, pyrolysis of the carbonaceous biomass particles produces 1) carbonaceous char and 2) volatile components vaporized into gas products. 2) Next, complete gasification of the carbonaceous char including lignin fractions produces 1) gaseous products including carbon monoxide, hydrogen, and tars as well as 2) greater than 99% pure carbonaceous ash. Next, 3) cracking of the tars, including larger hydrocarbons and aromatic compounds collectively known as tars, occurs at greater than 1000 degrees C. to the produce the substantial tar destruction to less than below 200 mg/m^3 and preferably less than 50 mg/m^3 and gasification of greater than 90 percent of the biomass particles into reaction products including hydrogen and carbon monoxide gas. The steps of at least the gasification and cracking of tars starts and finishes within the residence time of the biomass particles in the reaction zone in the chemical reactor between the range of 0.01 and 5 seconds. The pyrolysis may start with the low temperature 300 degree C. or less preheating by the carrier gas prior to entering the reactor tubes.

Some embodiments of the solar-driven chemical plant described herein include an opaque wall for each of the reactor tubes 202, 204, 206, 208. In such a system an inner wall of the receiver 200 and the reactor tubes 202, 204, 206, 208 may exchange energy primarily by radiation, not by convection or conduction. This can allow for the reactor tubes 202, 204, 206, 208 to achieve a fairly uniform temperature profile even though the concentrated solar energy is merely directly impinging on the reactor tubes 202, 204, 206, 208 from one direction. The radiation heat transfer from the inner wall and the reactor tubes 202, 204, 206, 208 may be the primary source of energy driving the gasification reaction in which the small biomass particles act as millions of tiny absorbing surfaces of radiant heat energy coming from the inner wall and the tubes.

Because of the high temperatures in the receiver cavity the materials used to make up a wall of the receiver cavity may have mechanical and chemical properties to maintain its strength at high temperatures (between 1100° C.-1500° C.). These materials can have very high emissivity or high reflectivity as well as high heat capacity and low thermal conductivity for the receiver cavity. Additionally, the material of the reactor tubes 202, 204, 206, 208 may possess high emissivity including 0.7 emissivity coefficient or better, high thermal conductivity including 30 watts per meter-Kelvin or better, at least moderate heat capacity of 8 joules per mole-degree Kelvin or better. Further, the material can be resistant to both the oxidizing air environment in the cavity as well as the reducing environment on the tube interior in order to allow the rapid gasification of dispersed falling biomass particulates. This can result in stable ash formation, complete amelioration of tar to less than 50 milligrams per normal cubic meter millimeter, and the production of the hydrogen and carbon monoxide products.

In some embodiments, the solar-driven chemical plant may include first and second reactor tubes of the multiple tubes 202, 204, 206, 208. The tubes 202, 204, 206, 208 can be materially made of refractory ceramics or metals. The material chosen must have good chemical stability and high strength at high temperatures (1100° C.-1500° C.). Additionally, material with high corrosion and abrasion resistance rates for the particle size of the biomass and steam concentration and good resistance to brittleness from solar flux may be selected. Good thermal shock resistance may provide protection from rapid changes in available solar energy. For example, the material chosen for tube construction is selected from the group of materials, individually or in combination, including silicon-carbide, Si/SiC composites, silicon-carbide coated graphite, Tungsten, molybdenum, mullite, zirconia, molybdenum with Aluminum Sulfide, Sintered submicron silicon carbide powder such as Hexoloy SA® SiC and Hexoloy SE® SiC, transparent and/or semi transparent sapphire, high aluminum content nickel-base alloys such as Haynes®

214, and refractory ceramics including aluminum oxide (Al2O3), ceramic matrix composites including melt infiltrated SiC/SiC, and other similar materials. Additionally, the materials may be used individually or in combination. The multiple reactor tubes may have one or more of an added 1) abrasion resistant coating, 2) heat resistant coating (>1050 degrees C.), and 3) corrosion resistant coating. The coatings may be added onto the reactor tubes and receiver cavity inner surfaces in a number of ways including sputtering, deposition, and other similar techniques.

In some embodiments, the material for the tubes may have high oxidation resistance at high temperatures if the receiver cavity is filled with a non-inert gas such as air. Some embodiments include material good at absorbing solar energy, high re-radiating properties via radiation emissivity, and high thermal conductivity. One such material may be silicon carbide protected graphite. The graphite may have thermo-mechanical properties required, such as high temperature capability, excellent thermal conductivity, very good thermal shock resistance and fracture toughness, and high emissivity. A coating of silicon carbide between 0.001" and 0.020" thick can provide oxidation resistance. This coating may be placed on the reactor tube through chemical vapor deposition or through direct siliconization of the graphite and the reactor tubes 202, 204, 206, 208 will be operated at wall temperatures between 1150° C. and 1400° C.

Thus, the reactor tubes may be made of silicon carbide coated graphite. The window of the receiver 200 can be made of sapphire and allows the cavity of the receiver 200 to be enclosed. An inert gas supply causes the volume in the receiver cavity to be flooded with an inert gas excluding oxygen from affecting the reactor tubes made of silicon carbide coated graphite.

The chemical reactor can also be constructed of a transparent material, allowing radiation emitted by the inner cavity wall of the receiver to pass directly through the containing reactor tube and impinge on the reactive particles. This tube could be constructed of any high temperature capable transparent material, and sapphire is a preferred material for this application. Sapphire or a sapphire-based compound has good high temperature properties, high transmission and low absorption in the visible and IR, making it well suited to this application.

In some examples, the solar-driven chemical plant may have length and diameter dimensions of a gasification reaction zone of each of the reactor tubes 202, 204, 206, 208 that may be sized to give a fast residence time of 0.01 second to 5 second at the gasification temperatures. A first of the multiple tubes may have a different diameter than a second of the multiple tubes. Additionally, the shape of each tube might be a cylindrical shaped pipe or a rectangular shaped pipe.

In some embodiments, a solar-driven chemical plant may include a downdraft geometry to the multiple reactor tubes 202, 204, 206, 208 in which the biomass particles fall through the downdraft reactor design with no need of disengagement of inorganic compounds or tars generated during the gasification reaction that can deposit downstream and foul critical system components. Accordingly, radiation heat transfer of the cavity walls and tubes surfaces will increase with a fourth power of temperature of the surfaces. At a temperature of greater than the 1000 degrees C. these high heat transfer rates may allow the biomass particles to achieve the high temperatures necessary for tar destruction and complete gasification in the very short residence times (0.01 s-5 s).

For example, the biomass particles may fall through the downdraft reactor to substantially eliminate an undesirable build-up of solid or liquid matter on the tube walls in the reaction zone which could lead to reduced heat transfer and even clogging of the tube because of the pressure and gravity pulling the particles through the reaction zone of the reactor tube. Additionally, low surface area to volume ratios may give less surface area for the material to stick on.

An average smallest dimension size between 50 microns (um) and 2000 um, with a general range of between 200 um and 1000 um may be used for the biomass particles. Additionally, because the surface area of the dispersed particles is so large as compared to the reactor tube surface area, radiant heat may be the primary means of heat transfer. Accordingly, in some embodiments, the use of these small particles gives an increased surface area to greatly increase the gasification reaction rate of the small biomass particles to facilitate the short residence times.

In some embodiments, the solar-driven chemical plant may include two or more feed lines in the multiple reactor tubes 202, 204, 206, 208. Each feed line may supply a reactor tube to control a dispersion pattern of the biomass particles into its corresponding reactor tube. This may be done to maximize radiation absorption by the particles when injected into the reactor tube based on a shape and width of the outlet of the feed line pipe carrying the biomass particles to its corresponding reactor tube.

Various embodiments include an insulation layer around the cavity of the indirect radiation driven geometry, absorbing cavity, and solar thermal receiver. Additionally, multiple reactor tubes 202, 204, 206, 208 may be located in the center of the cavity.

The thickness of the insulation can be set to control conductive heat losses. The cavity temperature and an average concentration of solar energy at the one or more apertures may control radiative losses. In some embodiments, an aperture design, orientation, and cavity working fluid (buoyancy) are set to control convective losses. The cavity at least partially enclosing the multiple reactor tubes 202, 204, 206, 208 acts like an oven. For example, the cavity may spread heat flux around through radiation and giving a much more even flux profile on the reactor tubes 202, 204, 206, 208 (azimuthally and axially) than the incident solar radiation has. Additionally, an averaging effect on the heat flux radiated from the absorbing cavity walls and multiple tubes occurs within the cavity.

An axis of the reactor tubes 202, 204, 206, 208 may include a heliostat solar field that focuses the moving Sun to shift the concentrated solar energy sunbeam weighting from West to East across the aperture. This solar energy sunbeam may impinge on the axis of the reactor tubes 202, 204, 206, 208 themselves through the course of each day. Additionally, the oven effect of the cavity along with the particles may tend to average energy amongst themselves at their design volumetric loadings. These volumetric loadings can combine to give the fairly uniform temperature profile and subsequent fairly uniform radial reaction profile of the biomass particles.

Additionally, the indirect radiation driven cavity reactor may have an aperture that is not covered with a window. In such a system, there is no need for a window (so no need to cool or keep such a window clean) and the reaction environment is sealed off from the cavity environment. While there is some efficiency loss for not directly irradiating the reacting solids, at high temperature, radiation heat transfer makes the required temperature difference very low (as it increases with temperature to the fourth power). The efficiency gains in not needing a window and rapid entrained flow kinetics far outweigh the indirect radiation losses. The solar energy from the array of heliostats may be directed onto tubes and in the reactor cavity where that energy is required. Note, the cavity, with absorbing walls and multiple tubes has advantages as stated herein.

A window, for example, is a solid transparent material that allows passage of selected wavelengths of radiation but not passage of solids, liquids, or gases and seals the receiver cavity as opposed to merely a viewing window not involved in the transmission of solar energy to the reactor tubes and cavity. Various embodiments of a solar-driven chemical plant may include a first window that is at least partially transparent to visible radiation but reflecting of IR radiation and no apertures. This can allow the re-radiation from the hot cavity to be trapped and redirected to the reactor tubes 202, 204, 206, 208, improving overall efficiency. Additionally, the window may be constructed of one or more of the following materials quartz, sapphire, tiled sheets of sapphire, or another suitable material and coated with any number of anti-reflective and reflective coatings to achieve the desired suite of reflective and transmissive properties. For example sapphire may be used as a material for the windows that enable the use of graphite material for multiple tubes, wherein the sapphire window may allow the receiver to be enclosed and the volume in the receiver cavity is flooded with an inert gas (e.g. N2 or Ar) excluding O2 from the graphite tubes.

In some examples of the systems and methods described herein, the solar-driven chemical plant can include length and diameter dimensions of a gasification reaction zone of each of the reactor tubes 202, 204, 206, 208, along with an arrangement and an amount of the tubes that may be matched to an amount of sun concentration from the heliostat field. This can give the residence time of 0.01 second to 5 seconds at the gasification temperatures. For example, a first of the multiple tubes may have a different diameter than a second of the multiple tubes. Tubes exposed to higher radiation fluxes (either direct or indirect), may be smaller in diameter, and tubes exposed to lower radiation fluxes (either direct or indirect) may be larger in diameter, thereby delivering the same particle heating rates with variable radiation fluxes. Additionally, the shape of each tube might be a cylindrical shaped pipe, a rectangular shaped pipe, or some other shaped pipe. Additionally, the reaction zone in the multiple tubes in which an inner atmosphere of the tubes/the reaction zone may be sealed from and not tolerant to oxygen from an environment present in the cavity.

Some embodiments may include a substantial axial length of the reactor tube. In this length, the biomass particles may be passed through the reaction zone of the reactor tube along a predetermined path. This path can be substantially coincident with the reactor tube axis. Additionally, the biomass particle reactants may be confined entirely within the reactor tube. In some examples, an arrangement of the cavity may cause high intensity radiant energy from the walls and tubes to be directed through the reactor tubes 202, 204, 206, 208 to coincide with the reaction zone of each reactor tube, either by absorption, conduction, and re-radiation (opaque tubes) or by transmission (transparent tubes).

Sufficient radiant energy may be absorbed in the reaction zone of the reactor tube to raise the temperature of the reactants to a level required to initiate and sustain the desired chemical reaction of the organic compound. Turbulent flow and/or possible buoyancy driven recirculation, both of which can happen in different operational regimes in the reactor tubes 202, 204, 206, 208 may be used. Additionally, turbulent flow has an average path that follows the axis of a reactor tube.

A solar-driven chemical plant may also include a chamber of the solar thermal receiver contains additional structures to the reactor tubes 202, 204, 206, 208, which have high temperature storage material that absorb the concentrated solar energy and are used one or more radiant heat masses to keep the reactor tubes 202, 204, 206, 208 hot during long periods of off sun, during cyclic up and down times in the plant, as well as keep radiant temperature in the reactor 200 more stable/less transient during normal operation.

In various embodiments, a solar-driven chemical plant may include an outer shell of a receiver that has one or more windows. In such an embodiment, an array of heliostats can focus concentrated solar energy thru the windows. Additionally, at least one of the windows may include a French window design with an air/gas curtain design having positive pressure blower or negative pressure vacuum. The windows may be made of sapphire material.

A solar-driven chemical plant may include a hood made of metal or ceramic that overhangs an aperture of the receiver cavity to minimize disruption of gas flow within the receiver. The receiver is the shell around the reactor tubes 202, 204, 206, 208, which the receiver absorbs or highly reflects solar flux to cause the radiant heat and then generally radiatively conveys that heat to the particles in the tubes of the reactor 200. Additionally, an aperture in the receiver cavity may be covered in very thin mesh made of transparent high temperature plastic or high heat resistance steel material to keep undesirable objects from entering the cavity from the environment.

The biomass particles may be fed to a multi-tube downdraft solar thermal receiver/reactor, in which the biomass is gasified in the presence of steam at a range of temperatures with the exit temperature exceeding 1000° C. An alternative design may include updraft reactor or fluid bed reactor. The receiver's use of an indirect radiation, absorbing cavity receiver with multiple tubular downdraft particle reactors is new to the solar thermal processing world (as well as the biomass gasification world).

Radiant heat transfer differs significantly from convective heat transfer and conductive heat transfer. In radiation heat transfer, both reflectivity and emissivity of materials are generally wavelength dependent. The temperature determines the wavelength distribution of the electromagnetic radiation as limited in intensity by Planck's law of black-body radiation. Thus, whether the radiation is coming from the Sun or a separate radiant heat source is a significant design consideration because the reflectivity and emissivity of the tube walls controls its ability to radiate the heat (radiant heat transfer) to the reacting particles or inert particles fed to transfer energy to a reactive gas.

Some embodiments may radiantly transfer heat in sufficient quantity in order to sustain the desired chemical reaction of the reactant gas, with the electromagnetic radiation coming from the Sun/solar radiation. Additionally, the receiver reactor may have an emissivity high in both the visible and IR ranges (0.3-10 micron wavelength).

An insulating cavity approach is essentially a blackbody cavity. Conductive losses can be controlled by changing the thickness of the insulation, and convective losses can be controlled through aperture design, orientation, and cavity working fluid (buoyancy). The key advantage of the blackbody cavity is control of the radiative losses, which are entirely determined by the cavity temperature and the average concentration at the aperture. The cavity acts like an oven, spreading heat flux around through radiation and giving a much more even flux profile on the reactor tubes 202, 204, 206, 208 (azimuthally and axially) than the incident solar radiation has. This is a major advantage for a solar field, where the moving sun shifts the beam from West to East weighting across the aperture through the course of each day.

In an embodiment, the amount of reactor tubes present in the cavity of the solar thermal receiver will be in a preferred range of 120-150 reactor tubes, with a range encompassing as few as 30 reactor tubes and as many as multiple 100s. Each reactor tube will have the same size diameter the rest of the reactor tubes. The geometric arrangement of the multiple reactor tubes relative to each other will be arc pattern with probably more than one row. The shape of each individual reactor tube will all be cylindrical. The expected size, shape, and orientation of the aperture in the receiver relative to the concentrated solar energy coming from the array of heliostats or solar concentrating dishes will be approximately a 7 meters by 7 m square. The length and diameter dimensions of the gasification reaction zone in the reactor tubes is the inner diameter of the tubes will be 6 inches and stretch the full length of the tube such as 9 meters long.

Figure 3:
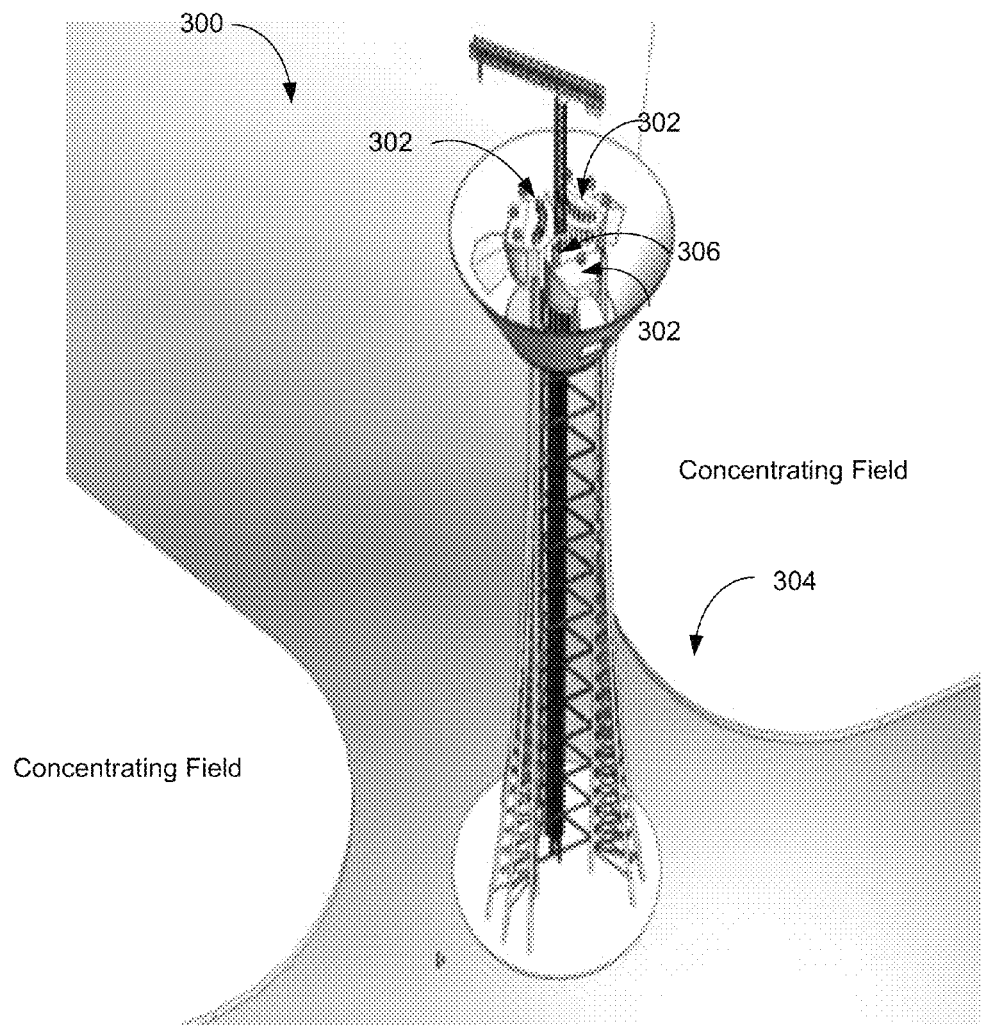
FIG. 3 illustrates a diagram of an embodiment of an example solar tower with receivers and heliostat field.

FIG. 3 illustrates a diagram of an example solar tower 300 with receivers 302 and heliostat field 304. A solar tower 300 may be used in the solar-driven bio-refinery with the entrained-flow biomass feed system. The feed system can be feedstock flexible via, for example, particle size control of the biomass.

Multiple solar thermal receivers 302 may be on a common tower 300. Each receiver 302 contains a chemical reactor 306. A chemical reactor 306 in each receiver 302 receives concentrated solar thermal energy from an array of heliostats 304 or concentrating dishes. The chemical reactor 306 can be, for example, a multiple reactor tube, downdraft, solar driven, chemical reactor 306, which receives concentrated solar thermal energy from the array of heliostats 306. The solar-driven bio-refinery may also include a biomass feed system that has the feed lines to each of the reactor tubes in a multiple tube chemical reactor 306. Biomass may be fed to the solar reactor 306 in an operation including three parts: biomass transport and preparation for feeding to the solar tower reactor 300, biomass transport to the top of the, e.g., 500+ foot tower, and distribution into the specific downdraft tubes of the reactor. The distribution may be performed via multiple stages.

The solar thermal gasifier has a downdraft geometry. The tubes are oriented vertically in the solar receiver cavity, and are, for example, 16" in inner diameter with, for example, a one inch, wall thickness to withstand at least 75 psig pressure on the inside tube walls.

An absorbing solar receiver cavity exists in which the gasification reactor tubes run vertically. Solar energy enters the cavity through an aperture open to the atmosphere and impinges on the reactor tubes and the cavity walls. The walls and tubes exchange energy primarily by radiation, allowing for the tubes to achieve a fairly uniform temperature profile even though solar energy is only impinging on the tubes from one direction.

An example receiver cavity is a sectioned cylinder, with an internal diameter of 10 m. The inside walls of the receiver cavity are constructed of refractory alumina plate. Outside of this plate layer can be alumina (or similar material) fiber insulation, which can have a thickness of, for example 24 cm. The receiver may be contained by a first structural carbon steel shell with a thickness of, for example, 0.090" wall thickness, where there is an air gap with a thickness of, for example, 2", beyond this first carbon steel shell. A second carbon steel shell of the same thickness as before may be used to form the boundary of the air gap. This second carbon steel shell may further contain the conductive losses from the cavity. The thickness of the insulation, air gap and steel shells has been designed so as to limit conductive losses from the cavity to less than 2% of the concentrated solar energy incident from the heliostat array on the aperture or window of the solar thermal receiver. The top and bottom surfaces of the cavity are similarly constructed.

In another example, the receiver 302 will ensure uniform distribution of energy across all the tubes. The tubes could all be of the same diameter and be fed by the same biomass feed rate, thereby all giving the same productivity. Similarly, the energy distribution may not be uniform across the receiver 302, yet the tubes are all to be fed with a same feed rate and give the same productivity. The way to achieve this would be to have tubes of different diameters, sized to deliver the same heat rates according to variable fluxes. The variability in the solar flux within the receiver 302 may also be addressed by controlling a corresponding variability in the individual feed rates through the equivalent tubes. Thus, many methods exist like the examples given above for changing the number, size diameter and length of the tubes and biomass feed rate per tube to address different flux environments.

The indirect simple tubular reactor design has a simple design, which is not only less difficult to design, but less likely to fail during operation. The feedstock flexibility clearly gives an economic advantage over processes that are limited to one or a few available feedstocks. By heating the reactor tubes with solar energy (which re-radiate to the particles), the problem of generating heat for the reaction and designing the reactor to conduct the reaction (essentially the endothermic/exothermic balancing problem) is eliminated. The solar energy can be directed to where it is required.

A falling particle reactor is an efficient way to get thermal energy into reacting solid particulates (or gases). Heat transfer from the reactor tubes to the reacting and/or non-reacting particles can occur by particle wall contact conduction, convection from the surrounding gas heated by the tube wall, or radiation from the tube wall or other surrounding particles. Even the heated non-reacting particles can be used for many purposes discussed in this document. At moderate temperatures, convection and conduction dominate when transferring energy to a fluid, but these require large amounts of surface area to be effective. To get around this problem, radiation heat transfer is required, which requires temperatures above 1000 degrees C. (and preferably above 1200 degrees C.). However, if the surface area being radiated to is small, local temperatures will get high and efficiencies will be low. A dispersed particle reactor solves this problem by greatly increasing the receiving surface area (it is essentially the surface area of the particles), shifting the limitation to the radiating tube. The particles tend to average energy amongst themselves at our volumetric loadings, giving a uniform radial reaction profile. If it is the gas that is desired to be heated (for steam reforming of methane or methane cracking, for example), inert particles can be used as radiation receivers and convection can be used to drive energy from the said particles to the gas. Because the surface area of the particles is so large (as compared to the tube surface area) and at a high temperature, the particle-to-gas convection heat transfer is no longer a limitation.

Additionally, the use of small particles increases the surface area for reaction. As reactions with gas phase components (e.g. steam, CO2) are surface area specific, the increased surface area greatly increases the reaction rate.

Note, in an embodiment, a heat transfer aid in the form of a particulate flow of inert particles may be used to heat the reactant gases. The flow of inert particles is passed through the chemical reactor through the riser of a circulating fluidized bed system. A fluidizing gas source supplies a reactant gas that entrains the inert particles and the particles of biomass flow upward through the reactor tubes. A return tube for the circulating fluidized bed then passes through the solar thermal receiver with some of the exit products. The reactant gas flows counter-currently or co-currently with the downward traveling inert particles and biomass particles.

In an embodiment, the flow of inert particles is mechanically metered and entrained in the gas flow and fed either upward or downward through the reactor tubes. A gas-solid separator such as a cyclone is coupled to the chemical reactor. The inert particles are mechanically separated from the product gas stream and recovered for reuse. The heat transfer aid used to heat the reactant gases can also be a non-circulating fluidized bed of inert particles in which the reactant gas is the fluidizing gas.

Another heat transfer aid may be in the form of a structured packing used to heat the reactant gases. The structured packing is one or more of the following: reticulate porous ceramic (RPC) foam, a ceramic monolith, or ceramic tubes inside each reactor tube. The packing can be configured for radiation as the primary mode of heat transfer to the heat transfer aids from the reactor tube walls. Conduction, convection, or some combination of the two is secondary modes of heat transfer.

Figure 4:
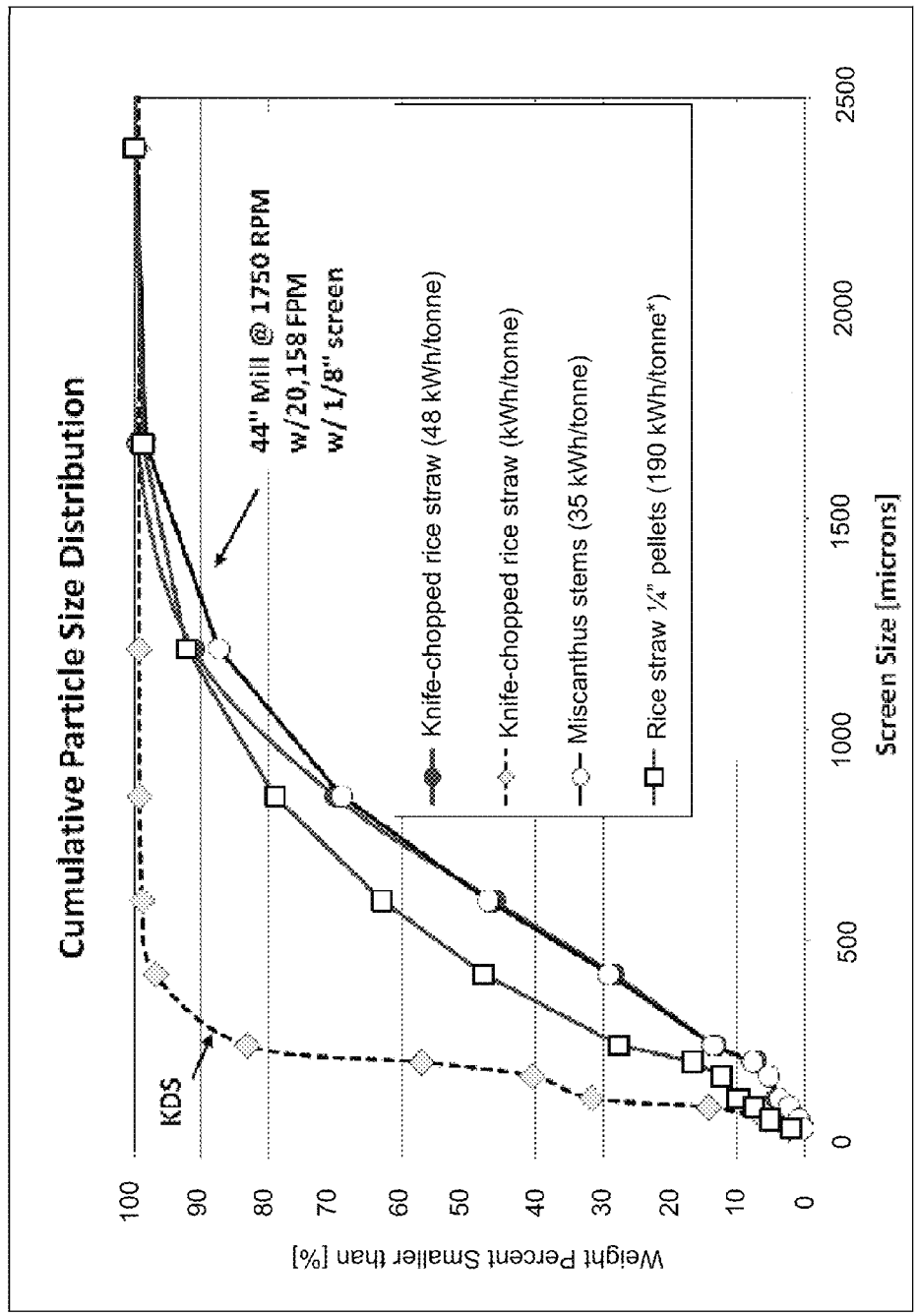
FIG. 4 illustrates a graph of an embodiment of particle size distribution of representative biomass material.

FIG. 4 illustrates a graph of cumulative particle size distribution. The graph illustrates the weight percentage below Y % for a given screen size in microns. Example materials are illustrated including knife-chopped rice straw and miscanthus stems. The smaller the size of the particle of the various types of biomass, the less difference in the way the feed system and reactor view particles from different types of biomass.

Figure 5:
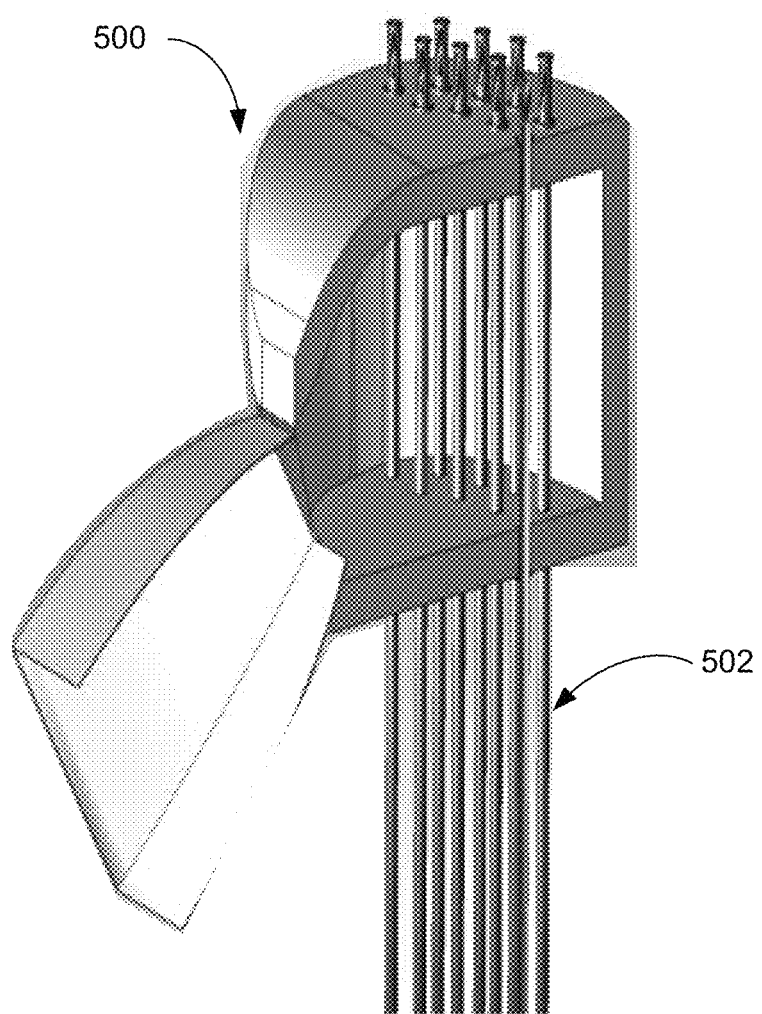
FIG. 5 illustrates a diagram of an embodiment of a solar thermal receiver with gasifier tubes.

FIG. 5 illustrates a diagram of a solar thermal receiver 500 with gasifier tubes 502. Solar thermal receiver 500 can form a portion of a solar-driven chemical plant. The feed system may feed biomass particles into the multiple reaction tubes 502, in which the particles of biomass may be gasified in the presence of steam at a temperature exceeding 950 degrees C. from an exit of a gasification reaction zone of the reactor tubes.

The solar driven chemical reactor that has multiple, for example, vertically oriented reactor tubes in a downdraft configuration, fluidized bed, or other reactor configuration.

As discussed, a window may be a solid transparent material that allows passage of selected wavelengths of radiation but impervious to solids, liquids, or gases, to pass the concentrated solar energy into the solar thermal receiver to impinge on the multiple reactor tubes and cavity walls of the receiver. The reactor tubes serve the dual functions of 1) segregating the biomass gasification reaction environment from the atmosphere of the receiver and 2) transferring solar energy by absorption and re-radiation, convection, and conduction. The energy transfer to the reacting particles can drive the endothermic gasification reactions of the particles of biomass flowing through the reactor tubes. Additionally, high heat transfer rates from the inner cavity walls through the tubes may allow the particles biomass to achieve a high enough temperature necessary for substantial tar destruction and complete gasification of greater than 90 percent of the carbon content of the biomass particles into reaction products including hydrogen and carbon monoxide gas in a very short residence time between a range of 0.01 and 5 seconds.

In some embodiments, the reactor uses the high surface area of the biomass particles to facilitate a rapid gasification reaction due to efficient heat and mass transfer. The gasification reaction is caused by the efficient heat transfer, which is a result of receiver configuration and temperature, and particle dispersion pattern.

The bio-refinery may produce fuels, chemicals, or both. For example, the integrated chemical plant may make fine chemicals from this bio-refinery as well as the liquid hydrocarbon fuel.

In some embodiments, the solar-driven chemical plant may include one or more open apertures or windows that might be part of an outer shell of the receiver. The receiver may at least partially enclose the multiple reactor tubes. Additionally, the inner wall of the receiver may absorb and highly reflect the concentrated solar energy from the array of heliostats to radiatively transmit that radiant heat to the biomass particles in the reactor tubes of the solar driven chemical reactor. In some embodiments, heat may transfer through the tube walls by conduction.

In some embodiments, a material making up the inner wall or at least coating the inner wall of the receiver cavity may have mechanical and chemical properties to retain its structural strength at high temperatures (between 1100° C.-1500° C.). This material may also have very high emissivity ($\epsilon > 0.8$) or high reflectivity ($\epsilon < 0.2$) as well as high heat capacity ($>200$ J/kg-K) and ($<1$ W/m-K) low thermal conductivity. The material for the reactor tubes may possess high emissivity ($\epsilon > 0.8$), high thermal conductivity ($>1$ W/m-K), and moderate to high heat capacity ($>150$ J/kg-K). Additionally, it may be resistant to the oxidizing air environment in the cavity and the reducing environment of the biomass gasification reaction in order to allow the rapid gasification of dispersed falling biomass particulates with a resultant stable ash formation.

Some embodiments may allow for amelioration of tar to less than 50 milligrams per normal cubic meter, and the production of the hydrogen and carbon monoxide products. Additionally, an inner wall of the receiver cavity may be made of or coated with an absorbing solar energy material rather than the highly reflective material.

For the cavity walls, some embodiments may use a material that has either very high emissivity or high reflectivity, low thermal conductivity, and high heat capacity. For the reactor tubes, some embodiments may use high emissivity, high thermal conductivity, and moderate to high heat capacity materials. Generally, the reactor tubes might need to be able to handle the oxidative environment on only one side and the steam plus reducing environment on the other. Additionally, usually only the reactor tubes need to withstand pressure. The receiver wall might only be oxidation resistant and strong enough so as not to fall apart under its own weight at temperature.

Figure 6A:
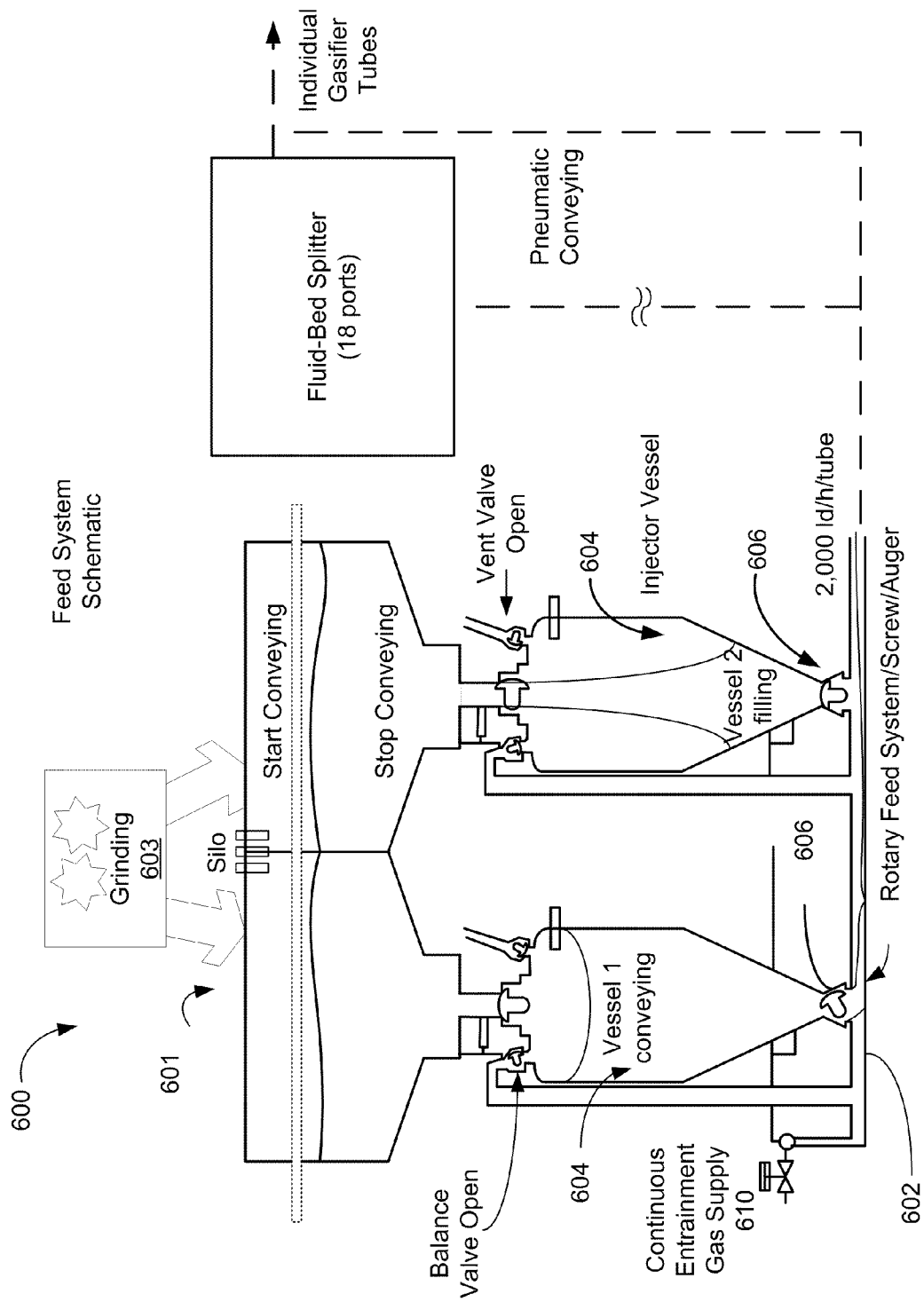

FIGS. 6a and 6b illustrate block diagrams of embodiments of the entrained-flow biomass feed system 600. Different types of feed systems may be used in conjunction with biomass into reactor, for example, drop tube, total solid fed into the reactor, slurry fed into the reactor, a moveable bed in the reactor, or combinations of these schemes.

One example solar-driven chemical plant may include an entrained-flow biomass feed system 600 that is preceded by a conveyer to bring bales of the biomass to a grinding system. The grinding system has a bale cutter/debaler, which debales the biomass. A mechanical cutting device then grinds the biomass into particles, which are to be fed into the solar driven chemical reactor. The grinding system supplies particles that have an average smallest dimension size between 200 microns (um) and 2000 um, with a general range of between 500 um and 1000 um to a lock hopper system 604 with a standard belt conveyer. The biomass particles are then fed across a pressure boundary into a pressurized entrainment gas for feeding into in the solar driven chemical reactor.

As illustrated in FIGS. 6a and 6b, the entrained-flow biomass feed system 600 can include a pressurized lock hopper 604 that feeds the biomass to a rotating metering feed screw 602 and then into an entrainment gas pipe at the lock hopper exit 606. The particles of the biomass are distributed into multiple entrainment gas lines by a flow splitter to feed the two or more reactor tubes making up the solar-driven chemical reactor. The entrainment gas for the entrained-flow biomass feed system may be a pressurized dry steam generated from waste heat recovered from either 1) the methanol/Methanol-To-Gasoline (MTG) units in the hydrocarbon fuel synthesis process or 2) the products from the gasification reaction in the solar driven chemical reactor.

Additionally, an entrained-flow biomass feed system having one or more feed lines to feed the biomass particles into the multiple reactor tubes, in which a separate entrainment line and metering device of the entrained-flow biomass feed system is used for each of the gasifier reactor tubes in the chemical reactor. This may allow for balancing of 1) amount of particles of biomass flowing through the feed line to each reactor tube to 2) an amount of solar energy available for that reactor tube in the multiple tube solar driven chemical reactor. Feed rate of the biomass particles can be controlled by the rotational rate of a feeding screw 602 at a base of the lock hopper 604, which responds to a feed demand signal received from the computerized control system based on the weight change of the biomass in the lock hopper monitored by a device such as load cells.

Thus, control of the rotational rate of the screw or auger 602 can move set amounts of biomass along the axis of rotation of the auger 602. The auger 602 may be located at the base of the lock hopper 604 and may be located at the base of the lock hopper and its rotational speed can be controlled by a computerized control system to respond to feed demand of the system. The control system hardware may be one or more of a Programmable Logic Controller, via different data communication protocols using Personal Computer, Macintosh, CNC, neural nets, analog devices, with accompanying software applications and algorithms scripted to perform various functions, or various combinations of these systems. In an embodiment, the computerized control system controls the feed rate of particles of biomass in the solar driven chemical reactor based on an amount of solar energy available indicated by sensors including temperature sensors and/or light meters.

Additionally, some systems may include a computerized control system configured to balance the amount of biomass particles flowing in each of the reactor tubes to an amount of solar energy available via, for example, a 2-phase control system. Such a system can be used to control flow in the individual reactor tubes by controlling a rotational rate of a screw/auger of a lock hopper feeding the biomass. Additionally, an amount of compression of a pinch valve configuration may be applied to a conduit such as a hose, tube, pipe, or other vessel capable of conveying materials section of each individual feed line that the biomass particles are flowing through to provide some control of flow, for example.

In some embodiments, a solar-driven bio-refinery may include an entrained-flow biomass feed system. The entrained-flow biomass feed system may be preceded by mechanical cutting device to grind and pulverize biomass to a particle size controlled to an average smallest dimension size between 50 microns (um) and 2000 um, with a general range of between 200 um and 1000 um. Additionally, the entrained-flow biomass feed system may supply a variety of biomass sources fed as particles into the solar driven chemical reactor without changing the reactor's structure. (In some examples, non-food stock biomass might be used.) Additionally, the variety may include three or more types of biomass that can be fed, individually or in combinational mixtures, from the group consisting of rice straw, rice hulls, corn stover, switch grass, non-food wheat straw, miscanthus, orchard wastes, sorghum, forestry thinning, forestry wastes, energy crops, source separated green wastes and other similar biomass sources. The biomass may be in a raw state or partially torrefied state, as long as a few parameters are controlled including particle size of the biomass and operating temperature range of the reactor tubes. A mechanical agitator in the lock hopper or feeding vessel can be used to enhance the bulk flow of biomass particles that might otherwise tend to bridge in the vessel due to Van der Waal's forces.

The reactor tubes are configured to generate syngas from one or more of the following: (i) biomass particles and steam (ii) biomass particles, methane, and steam, (iii) methane and steam (SMR). The different reactor tubes within the same receiver are configurable to operate with the different chemical reactants listed above. Also, at least two or more different types of biomass materials might be used in the same reactor tube geometry in some example systems. This can obviate any need for a complete reengineering when a new type of biomass feedstock is used. It will be understood that multiple feed stocks could be used simultaneously or one feedstock might be used at a time.

Figure 7:
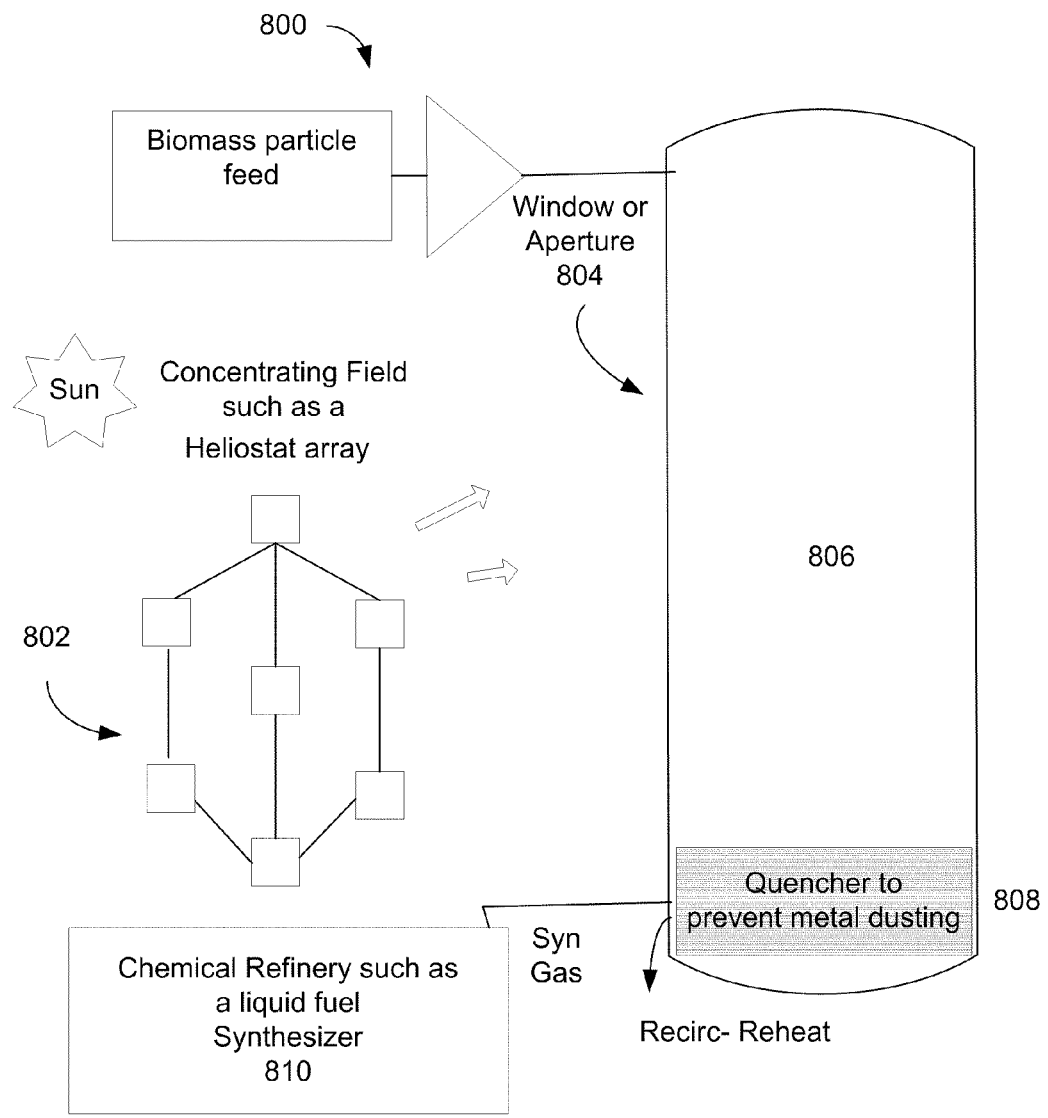
FIG. 7 illustrates a diagram of an embodiment of a solar-driven bio-refinery.

FIG. 7 illustrates a diagram of a solar-driven chemical refinery 800. In such a system, solar power 802 passes through a window or open aperture 804 to heat a reactor chamber 806. A quencher 808 may be used to prevent undesired reactions. As illustrated, biomass particles flow into the system at 810 and syngas flows out. Additionally, a heat exchange may occur between the biomass particles and the syngas.

Some embodiments of the solar-driven chemical plant may include insulation on an outside shell of the receiver to reduce heat loss during operations and overnight during shutdown. The insulation may be thick enough to keep conductive losses to less than 10% during operations. Examples of insulation that might be used include one or more from the group consisting of ceramic brick, ceramic blanket, and combinations of the two.

In various embodiments a small boiler or resistance heaters may be connected to the outside wall of the receiver shell of the receiver to aid in temperature control of the chemical reactor. The boiler or heater may aid in temperature control during operations, as well as during shutdown and start up operations.

In some examples a quench zone may be included immediately downstream of the exit of the chemical reactor to immediately and rapidly cool at least the hydrogen and carbon monoxide reaction products. This cooling may occur within 2-10 seconds of exiting the reactor, for example. The cooling may be to a temperature below a level at which undesired chemical reactions occur at negligible rates.

A return tube may also exist at the exit of the chemical reactor. The return tube passes outside the receiver for the multiple reactor tubes to recycle all or a portion of the products of the gasification reaction from the exit of the chemical reactor.

The array of heliostats 802 can be used to focus light onto a window 804 to the reactor 806. In reactor 806 biomass particles can be reacted away to syngas, which in turn can be synthesized into liquid fuel in liquid fuel synthesizer 808.

Some embodiments of the solar-driven chemical plant may be configured such that, at an exit of the gasification reaction zone in the reactor tubes of the chemical reactor, the biomass gasification products from the multiple tubes may be joined into several large tubes. Additionally, then water or methanol is injected into the large tubes to rapidly cool the product gases and, in the case of water injection, provide steam for the water gas-shift reaction necessary to achieve a proper H2 to CO ratio between 2.0 and 2.7 for syngas used by the on-site fuel synthesis reactor in the fuel synthesis process.

In some embodiments, a high solar flux concentration from the heliostat field may provide or give equal to or greater than three MW per meters squared of solar energy at the apertures. This may give the receiver cavity a capacity of at least 2000 kW and generally around 60,000 kW. The multiple tube construction of the cavity may increase the surface area for radiative transfer to the biomass particles. Additionally, the shape of the reactor tubes may be substantially rectangular, which also yields a higher surface area for equivalent volume than cylindrical shaped tubes.

As the gasification is performed through indirect heating, the cavity and tube walls must be able to efficiently transfer solar energy to the reacting particles. Residence times greater than 2 seconds will be more than sufficient for the biomass to be gasified at temperatures between 500° C. and 1000° C. The key limiting factor in receiver design is heat transfer from the indirectly heated cavity wall and the reacting particulates.

Some embodiments of a solar-driven chemical plant may include inert heat absorbing particles. Some examples of such particles may include silica, Carbo HSP, or other proppants. These can be entrained along with the biomass particles and heat energy to drive the chemical gasification reaction of the biomass particles comes from the following three sources 1) the heat absorbing particles, 2) the reactor tubes, and 3) an inner wall of the cavity and all that heat energy is derived from the concentrated solar energy. Additionally, an ash and particle storage mechanism may be used. In such a mechanism, the inert heat absorbing particles and ash remnants of the biomass exit the solar reactor at the greater than 1000 degrees C.

Some embodiments may also include a gas-solid separator. The separator can be configured to separate the inert heat absorbing particles and ash remnants from the gas products that then can be transferred into the ash and particle storage system. The particle storage system may store these particles and ash remnants to recover their heat in order to heat a working fluid that drives an electricity generation apparatus or other apparatus used in operating heat based processes. Examples of such heat recuperation include preheating water, preheating gas streams, and other thermodynamic work.

Figure 8:
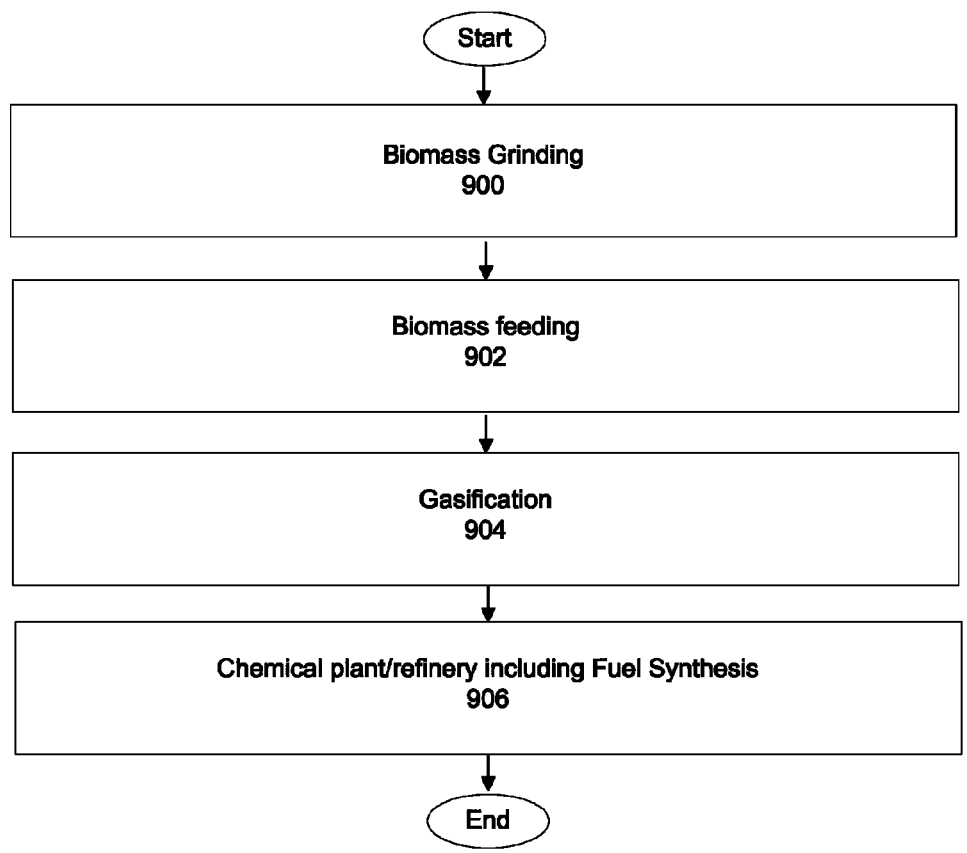
FIG. 8 illustrates flow diagram of an embodiment of the system.

FIG. 8 illustrates a flow diagram of an embodiment of the system. In step 900, biomass grinding can occur. Equipment generally used for grinding biomass includes impact mills (e.g. hammer mills), attrition mills, and kinetic disintegration mills (e.g. flail mills). A hammer mill system can be used to grind debaled biomass into particles, which are to be fed into the solar thermal gasifier. The ground biomass particles have an average smallest size between 500 um and 1000 um, and are loaded into the lock hopper system with a standard belt or vacuum conveyer.

In step 902 biomass feeding occurs. In some embodiments, high pressure feeding may be used. High pressure feeding of solids of biomass with gasification at pressure may reduce capital cost due to the ability to use smaller compressors in some such systems. Additionally, operating cost may be reduced because energy for pressurizing carrier gas comes from the sun, as opposed to from electricity. The lock hopper system can feed the reactor processes at pressure. For example, the feeding system can entrain the biomass materials in steam at high pressure, successfully disengage the particulates in the cyclone system, and distribute flow appropriately to the reactor tubes.

In step 904 gasification occurs. For example, in some embodiments, concentrated solar thermal energy drives gasification of the particles of the biomass to generate at least hydrogen and carbon monoxide products from the gasification reaction.

In step 906 fuel synthesis occurs. An on-site fuel synthesis reactor can receive the hydrogen and carbon monoxide products from the gasification reaction and use the hydrogen and carbon monoxide products in a hydrocarbon fuel synthesis process to create a liquid hydrocarbon fuel.

The methods and apparatuses of the invention in some cases may be implemented using computer software. If written in a programming language conforming to a recognized standard, sequences of instructions designed to implement the methods can be compiled for execution on a variety of hardware platforms and for interface to a variety of operating systems. It will be appreciated that a variety of programming languages may be used to implement the teachings of the invention as described herein. Furthermore, it is common in the art to speak of software, in one form or another (e.g., program, procedure, application, driver, etc.), as taking an action or causing a result. Such expressions are merely a shorthand way of saying that execution of the software by a computer causes the processor of the computer to perform an action or produce a result.

A machine-readable medium is understood to include any mechanism for storing or transmitting information in a form readable by a machine (e.g., a computer). For example, a machine-readable medium includes read only memory (ROM); random access memory (RAM); magnetic disk storage media; optical storage media; flash memory devices, etc.

While some specific embodiments of the invention have been shown the invention is not to be limited to these embodiments. The invention is to be understood as not limited by the specific embodiments described herein, but only by scope of the appended claims.

We claim:

1. A chemical plant, comprising:
a source of biomass particles;
a source of carrier gas;
a heat source;
a thermal receiver having an inner cavity with cavity walls which is configured to receive concentrated energy from the heat source to cause a radiant heat within the inner cavity;
a radiant heat driven chemical reactor comprising multiple reactor tubes, each reactor tube having an outer wall; and
wherein the outer walls of the multiple reactor tubes are comprised of material configured to 1) segregate the particles of biomass being gasified in an endothermic gasification reaction environment from an atmosphere of the inner cavity and 2) transfer energy exchanged with the inner cavity by primarily absorption and re-radiation, as well as secondarily through convection and conduction to the reacting particles to drive the endothermic gasification reaction of the particles of biomass flowing through the multiple reactor tubes;
wherein the multiple reactor tubes are fluidly connected to the source of biomass particles and the source of carrier gas such that the particles of biomass are gasified in a presence of the carrier gas in the endothermic gasification reaction to produce hydrogen and carbon monoxide products at an exit temperature from the multiple reaction tubes exceeding 1000 degrees C.;
wherein the cavity walls and the multiple reactor tubes are made of materials configured to allow the particles of biomass to achieve a high enough temperature necessary for substantial tar destruction to less than 200 mg/m^3 and gasification of greater than 90 percent of a carbon content of the particles of biomass into reaction products including the hydrogen and the carbon monoxide gas in a residence time of greater than 0.01 second;

wherein at least two of the multiple reactor tubes are materially made of refractory ceramics or metals, wherein the material of the refractory ceramics or the metals chosen have a chemical stability and a strength suitable for operation at temperatures between 1000-1600 degrees C., corrosion and abrasion resistance rates suitable for the operation at the temperatures between 1000-1600 degrees C., a radiation emissivity ($\epsilon$) greater than 0.8, a thermal conductivity greater than 1 W/m-K, and be suitable for operation at pressures up to 75 PSIG; and wherein the material chosen for the multiple reactor tubes is selected from the group of materials, individually or in combination, including silicon-carbide, silicon-carbide coated graphite, Tungsten, molybdenum, mullite, zirconia, molybdenum with Aluminum Sulfide, Sintered submicron silicon carbide powder, ceramic matrix composites including melt infiltrated SiC/SiC, high aluminum content nickel-base alloys, and refractory ceramics including aluminum oxide ($Al2O3$).

2. The chemical plant of claim 1, further comprising:
a top of the multiple reactor tubes, wherein the tubes are oriented vertically within the inner cavity, and the source of the biomass particles is coupled to the chemical reactor so as to introduce the biomass particles at the top of the multiple reactor tubes, entrained by the carrier gas, and the biomass particles are directed by gravity and pressure through a gasification reaction zone of the multiple reactor tubes, where temperatures of operation are clearly delineated with the receiver cavity wall temperatures between 1000 degrees C. and 1600 degrees C. and the exit temperature from the multiple reactor tubes exceeds 1000 degrees C. but not 1600 degrees C.

3. The chemical plant of claim 1, further comprising:
an on-site methanol reactor comprising an input connected downstream to the radiant heat driven chemical reactor to receive the hydrogen and carbon monoxide products from the endothermic gasification reaction, wherein the on-site methanol reactor is configured to use the hydrogen and carbon monoxide products in a hydrocarbon synthesis process to create a hydrocarbon or hydrocarbons; and wherein the multiple reactor tubes each has an inner diameter sized to provide a substantially uniform gasification of the biomass particles from an edge to a center of the tube, and has a thickness of the outer wall selected to withstand the pressure up to 75 PSIG at 1400 degrees C. on an inside of the outer wall.

4. The chemical plant of claim 1, wherein the inner cavity walls absorb or highly reflect the concentrated energy from the heat source to cause the radiant heat and then generally radiatively transmits the radiant heat to the biomass particles in the multiple reactor tubes, and the inner cavity walls are made of a material to allow the inner cavity to be operated at a wall temperature greater than 1200 degrees C. to enable the high heat transfer rates, rapid reaction kinetics of the residence time, and high selectivity of the carbon monoxide and hydrogen produced from the biomass gasification reaction for syngas.

5. The chemical plant of claim 1,
wherein the inner cavity walls and the multiple reactor tubes exchange energy primarily by radiation, not by the convection or the conduction, allowing for the multiple reactor tubes to achieve a fairly uniform temperature profile even though heat energy primarily impinges on the reactor tubes from one direction, and wherein the radiation heat transfer from the inner cavity walls and the multiple reactor tubes is a primary source of energy driving the gasification reaction in which the small biomass particles act as tiny absorbing surfaces of radiant heat energy coming from the inner cavity walls and the multiple reactor tubes; and wherein a shape of each of the multiple reactor tubes is a cylindrical shaped pipe, at least 30 reactor tubes are present in the inner cavity, and a geometric arrangement of the multiple reactor tubes relative to each other is an arc pattern.

6. The chemical plant of claim 1,
wherein the materials making up the inner cavity walls have mechanical and chemical properties to withstand the temperatures between 1000-1600 degrees C., have an emissivity ($\epsilon$) greater than 0.8 or a reflectivity ($\epsilon$) less than 0.2 as well as a heat capacity greater than >200 J/kg-K and the thermal conductivity less than 1 W/m-K, and wherein the material making up the multiple reactor tubes possesses a thermal conductivity of 30 watts per meter-Kelvin or better, a heat capacity of at least 8 joules per mole-degree Kelvin or better, and is resistant to both an oxidizing air environment within the inner cavity of the thermal receiver and a reducing environment on an interior of the multiple reactor tubes in order to allow within the multiple reactor tubes the gasification of dispersed falling biomass particles with a resultant stable ash formation, amelioration of tar to less than 50milligrams per normal cubic meter, and a production of the hydrogen and carbon monoxide products at operating temperatures within the multiple reactor tubes between 1000-1600 degrees C.

7. The chemical plant of claim 6, wherein the inner cavity walls of the thermal receiver are constructed of refractory alumina plate within alumina fiber insulation, which is contained within a first structural carbon steel shell.

8. The chemical plant of claim 1, further comprising:
wherein the multiple reactor tubes are made of SiC coated graphite; and
an inert gas supply is coupled to the inner cavity so as to flood the inner cavity with an inert gas so as to prevent oxygen from affecting the SiC coated graphite.

9. The chemical plant of claim 1, wherein an oxidation resistance suitable for the operation at temperatures between 1000 degrees C. and 1600 degrees C. is provided by a coating of silicon carbide, between 0.001" and 0.02041 thick, placed on the multiple reactor tubes through chemical vapor deposition or through direct siliconization of graphite, and wherein the multiple reactor tubes are arranged in a geometrical configuration relative to one another within the inner cavity of the thermal receiver where the geometrical configuration comprises either a cylindrical or rectangular pattern.

10. The chemical plant of claim 1, wherein a length and diameter dimensions of a gasification reaction zone of each of the multiple reactor tubes is sized to give a residence time of greater than 0.01 second at gasification temperatures, and a first of the multiple reactor tubes has a larger diameter than a second of the multiple reactor tubes, and shape of each tube is either a cylindrically shaped pipe or a rectangular shaped pipe.

11. The chemical plant of claim 1, further comprising:
an entrained-flow biomass feed system comprising two or more feed lines connected to a top of the multiple reactor tubes so as to feed the particles of biomass into the multiple reactor tubes, wherein a separate entrainment line and metering device of the entrained-flow biomass feed system is used for each of the multiple reactor tubes, which provides a balancing of factors including 1) an amount of particles of biomass flowing through the feed line connected to each of the multiple reactor tubes and 2) an amount of energy available from the heat source for each of the multiple reactor tubes; and a computerized control system programmed to balance the amount of biomass particles flowing to each of the multiple reactor tubes and the amount of energy available from the heat source for each of the multiple reactor tubes.

12. The chemical plant of claim 1, further comprising:

an entrained-flow biomass feed system connected to the multiple reactor tubes comprising a reduction mechanism which reduces the biomass to a particle size controlled to an average smallest dimension size between 50 microns (um) and 2000 um, with a general range of between 200 um and 1000 um;

wherein the entrained-flow biomass feed system supplies different types of biomass sources fed as particles into the multiple reactor tubes without requiring change in a structure of the radiant heat driven chemical reactor, wherein the different types of biomass sources comprise forestry wastes and other similar biomass sources in a partially torrefied state, as long as a few parameters are controlled including the particle size of the biomass and an operating temperature range of the multiple reactor tubes.

13. The chemical plant of claim 1, further comprising:

an entrained-flow biomass feed system having one or more feed lines to feed the biomass particles into the multiple reactor tubes, in which a separate entrainment line and metering device of the entrained-flow biomass feed system is used for each of the multiple reactor tube;

wherein the multiple reactor tubes are comprised of said material suitable to withstand the temperatures up to 1600 degrees C. and retain their structural strength, to resist an oxidative environment on one side exposed to the inner cavity of the thermal receiver via an addition of a coating, resistant to steam and a reducing environment on the other side in which the gasification reaction occurs, and pressure resistant up to 75 PSIG.

14. The chemical plant of claim 1, wherein the material for the multiple reactor tubes includes, SiC coated graphite, Si/SiC composites, and ceramic matrix composites including melt infiltrated SiC/SiC, wherein the multiple reactor tubes have one or more of an added 1) abrasion resistant coating, 2) heat resistant coating suitable for temperatures greater than 1050 degrees C., and 3) a corrosion resistant coating, and wherein the coatings are added onto the multiple reactor tubes and the inner cavity inside surfaces via sputtering, deposition, or any combination of both.

* * * * *